US012599642B2

(12) United States Patent
Fernandez et al.

(10) Patent No.: US 12,599,642 B2
(45) Date of Patent: Apr. 14, 2026

(54) **COMPOSITIONS DERIVED FROM *SALVIA HISPANICA* SEEDS**

(71) Applicant: Signum Biosciences, Monmouth Junction, NJ (US)

(72) Inventors: Jose Fernandez, Monmouth Junction, NJ (US); Eddie Perez, Monmouth Junction, NJ (US); Kristen Huber, Monmouth Junction, NJ (US); Jason Healy, Monmouth Junction, NJ (US); Corey Webb, Monmouth Junction, NJ (US); Karl Rouzard, Monmouth Junction, NJ (US); Mike Voronkov, Monmouth Junction, NJ (US); George Nikonov, Monmouth Junction, NJ (US)

(73) Assignee: SIGNUM BIOSCIENCES INC, Monmouth Junction, NJ (US)

( * ) Notice: Subject to any disclaimer, the term of this patent is extended or adjusted under 35 U.S.C. 154(b) by 464 days.

(21) Appl. No.: 17/909,387

(22) PCT Filed: Mar. 4, 2021

(86) PCT No.: PCT/US2021/020830
§ 371 (c)(1),
(2) Date: Sep. 4, 2022

(87) PCT Pub. No.: WO2021/178639
PCT Pub. Date: Sep. 10, 2021

(65) Prior Publication Data
US 2023/0111153 A1     Apr. 13, 2023

Related U.S. Application Data

(60) Provisional application No. 62/984,960, filed on Mar. 4, 2020.

(51) Int. Cl.
*A61K 36/537*     (2006.01)

(52) U.S. Cl.
CPC ........ *A61K 36/537* (2013.01); *A61K 2236/15* (2013.01); *A61K 2236/33* (2013.01); *A61K 2236/37* (2013.01); *A61K 2236/51* (2013.01); *A61K 2236/53* (2013.01)

(58) Field of Classification Search
CPC .............. A61K 36/537; A61K 2236/15; A61K 2236/33; A61K 2236/37; A61K 2236/51; A61K 2236/53; A61K 8/9789; A61K 2236/00; A61K 9/0014; A61Q 19/00; A61Q 17/04; A61P 17/00; A61P 17/06; A61P 25/00; A61P 25/28; A61P 31/04
See application file for complete search history.

(56) References Cited

U.S. PATENT DOCUMENTS

| | | | |
|---|---|---|---|
| 9,532,965 B2 | 1/2017 | Minatelli et al. | |
| 2006/0281814 A1 | 12/2006 | Angers et al. | |
| 2012/0076876 A1 | 3/2012 | Qu et al. | |
| 2013/0136708 A1* | 5/2013 | Qu ........................ | A61K 8/345 424/746 |
| 2014/0154194 A1 | 6/2014 | Rana et al. | |

FOREIGN PATENT DOCUMENTS

CN          106562428 A      4/2017

OTHER PUBLICATIONS

Flavourtech, Centritherm® Evaporator, 2016, 5 pages. Accessed on Dec. 3, 2024. Available online: <https://flavourtech.com/products/centritherm-evaporator/>. (Year: 2016).*
Dunford, N., Oil and Oilseed Processing II, 2016, Oklahoma State University Extension, 9 pages. Accessed on Dec. 3, 2024. Available online: <https://extension.okstate.edu/fact-sheets/oil-and-oilseed-processing-ii.html>. (Year: 2016).*
Li, J., et al., Extractive Distillation with Ionic Liquid Entrainers for the Separation of Acetonitrile and Water, 2019, Ind Eng Chem Res., 58:5602-5612, 11 pages. <http://dx.doi.org/10.1021/acs.iecr.8b05907>. (Year: 2019).*
Matyash, V., Lipid extraction by methyl-tert-butyl ether for high-throughput lipidomics, 2008, J of Lipid Res., 49(5):1137-1146, 10 pages. <https://doi.org/10.1194/jlr.d700041-jlr200>. (Year: 2008).*
PubChem, Methyl tert-buytl ether, 2024, National Library of Medicine, Accessed on Dec. 4, 2024. Available online: <https://pubchem.ncbi.nlm.nih.gov/compound/Methyl-tert-butyl-ether>. (Year: 2024).*
Schaufler, D., Oilseed Fact Sheet: Oil Filtration, 2013, Penn State Extension, 7 pages, Accessed on Dec. 4, 2024. Available online: <https://www.sare.org/wp-content/uploads/Oil-Filtering-Fact-Sheet.pdf>. (Year: 2013).*
Brooks, D.D., Silica Hydrogel and its Use in Edible Oil Processing, 2019, AOCS Lipid Library, 12 pages, Accessed on Dec. 4, 2024. Available online: <https://lipidlibrary.aocs.org/edible-oil-processing/silica-hydrogel-and-its-use-in-edible-oil-processing>. (Year : 2019).*
Mariana Grancieri et al. "Comprehensive reviews in food science and food safety // Chia Seed (*Salvia hispanica* L. ) as a source of proteins and bioactive peptides with health benefits: a review". 2019, p. 483.
Grzegorz Dabrowski et al, Supercritical CO2extraction in chia oils production: impact of process duration and co-solvent addition, Food and Sci Biotechnology, The Korea Soc. of Food and Science Technology, Heidelberg, vol. 27, No. 3, Jan. 17, 2018, pp. 677-686, XP036521954, ISSN: 1226-7708, DOI: 10.1007/S10068-018-0316-2 [retrieved on Jan. 17, 2018].
Grzegorz Dabrowski et al, Composition and oxidative stability of oil from *Salvia hispanica* L. seeds in relation to extraction method, European Journal of Lipid Science Technology, Wiley VCH Verlag, Weinheim, DE, vol. 119, No. 5, Nov. 11, 2016, p. n/a, XP072144209, ISSN: 1438-7697, DOI 10.1002/EJLT. 201600209. J. Lipid Sci. Technol. 2017, 119, 1600209.

(Continued)

*Primary Examiner* — Aaron J Kosar
*Assistant Examiner* — Jennifer Lynn Cain
(74) *Attorney, Agent, or Firm* — Kim IP Law Group LLC

(57) ABSTRACT

Methods of preparing a composition from chia seeds are provided. Compositions, including compositions prepared by the presently disclosed methods, and methods regarding selecting chia seeds and administering chia seed extracts are also disclosed.

18 Claims, 5 Drawing Sheets

(56)     References Cited

OTHER PUBLICATIONS

Maria V. Calvo et al, Appraisal of the stability of two-stage extraction process by combining compressed fluid technologies of polar lipid fractions from chia seed, Food Research International , Elsevier, Amsterdam, NL, vol. 131, Jan. 22, 2020, XP086115710, ISSN: 0963-9969, DOI: 10.1016/J. Foodress. 2020.109007 [retrieved on Jan. 22, 2020].

Vanesa Y. Ixtaina et al, Characterization of chia seed oils obtained by pressing and solvent extraction, Journal of Food Composition and Analysis, Elsevier, Amsterdam, NL, vol. 24 No. 2, Aug. 18, 2010 pp. 166-174, XP028184634, ISSN:0889-1575, DOI 10.1016/ J.JFCA.2010.08.006 [retrieved on Dec. 7, 2010].

Joanna Kobus-Cisowska, et al, "In vitro screening for acetylcholinesterase and butyrylcholinesterase inhibition and anti-microbial activity of chia seeds (*Salvia hispanica*)", Electronic Journal of Biotechnology, vol. 37, Jan. 2019, pp. 1-10, XPO55854874.

Ricardo Ayerza, "The seeds protein and oil content, fatty acid composition, and growing cycle length of a single genotype of Chia (*Salvia hispanica* L.) as affected by environmental factors". Journal of oleo science, vol. 58, No. 7, 2009, pp. 347-354, XP055854878

European Search Report in International Patent Application No. PCT/US2021/020830, dated Jul. 24, 2024.

Extended European Search Report in International Patent Application No. PCT/US2021/020830, dated Jul. 24, 2024.

\* cited by examiner

COMPOSITIONS DERIVED FROM *SALVIA HISPANICA* SEEDS

CROSS-REFERENCE TO RELATED APPLICATIONS

This is a national stage application filed under 35 U.S.C. § 371 of International Patent Application No. PCT/US2021/020830, filed Mar. 3, 2021, which claims benefit to U.S. Provisional Patent Application No. 62/984,960 filed on Mar. 4, 2020.

FIELD OF THE INVENTION

The present invention relates to compositions containing compounds extracted from chia seeds, as well as methods for making and using these compositions. The present invention also relates formulations of chia compositions that have improved color uniformity and stability. The present invention, moreover, relates to methods of assessing or estimating the ability of composition to inhibit the PP2A demethylation activity of a PP2A demethylating enzyme.

BACKGROUND

Chia, a species of flowering plant in the mint family, is grown commercially for its seeds that are rich in omega-3 fatty acids (58-64% of total lipids; 31-35% lipids by mass of the seed). Chia is an annual herb growing up to 1.75 meters tall, with opposite leaves that are 4-8 cm long and 3-5 cm wide. Its flowers are purple or white and are produced in numerous clusters in a spike at the end of each stem. Chia is hardy from USDA Zones 9-12, and is typically grown commercially in its native Mexico and Guatemala, as well as Bolivia, Ecuador, Nicaragua, Uruguay, Argentina, Australia, and southwestern United States.

As used colloquially, "chia" generally refers to *Salvia hispanica* or *Salvia columbariae*. However, many plants cultivated as *Salvia hispanica* are in fact *Salvia lavandulifolia* (also known as Spanish sage), a small woody herbaceous perennial native to Spain and southern France, growing in rocky soil in Maquis shrubland. For purposes of the present application, the term "chia" shall refer to *Salvia hispanica*.

Today, chia is grown and consumed commercially. New varieties of chia have been bred in for improved characteristics. Examples of improved chia varieties include the Sahi Alba 914 variety (developed in Argentina by TFSB LLC), the 65 Heartland variety (developed by the University of Kentucky) and the Rehnborg variety (developed by Access Business Group International and deposited under ATCC Patent Deposit Designation PTA-124758). See, e g., U.S. Pat. Nos. 8,586,831; 9,686,926; 10,357,006.

While the nutritional benefits, and even the cosmetic and skincare benefits, of chia and chia-based products have long been recognized, what has not heretofore been known is the importance of protein phosphatase 2A (PP2A) modulation activity as an important criterion for selecting the chia plant variety that is the source of the chia composition or product, and the importance of optimizing PP2A demethylation activity in developing extraction, manufacturing and formulation methods for chia compositions and products.

PP2A

Protein phosphatase 2A (PP2A), a major serine/threonine phosphatase, has been implicated in a broad range of cellular functions anywhere from development to disease. Consisting of a scaffolding (A), regulatory (B) and catalytic (C) subunit, this trimeric holoenzyme is highly regulated through structural assembly, post-translational modifications and small molecule interactions. Methylation Of PP2A's carboxy-terminal tail has not only been implicated in modulating its activity and specificity but it has also been shown to be of particular importance in neurodegenerative diseases such as Alzheimer's and Parkinson's disease, It has been established that decreased PP2A activity can contribute to tau hyperphosphorylation, which is a critical event in the development of Alzheimer's type dementia. For this reason, modulators of PP2A's methylation state are of particular importance.

PP2A methylation is controlled by a specific S-adenosylmethionine (SAM) dependent methyltransferase and a specific methylesterase. Methylation modulates PP2A activity by controlling the association of regulatory B subunits with the catalytic AC core.

Homocysteine, a sulfur-containing amino acid that can be either remethylated to methionine or undergo a trans-sulfuration reaction to cystathionine, plays a key role in methylation metabolism. The conversion of homocysteine to methionine occurs in all tissues. Methionine is activated by ATP in the presence of methionine adenosyl transferase to form the methyl donor, S-adenosylmethionion ("SAM"). SAM-dependent methylation reactions in the presence of SAM-dependent methyltransferases result in the formation of S-adenosylhomocysteine ("SAH"), which is cleaved by SAH hydrolase to form adenosine and homocysteine.

Data in the clinical literature shows a significant correlation between elevated plasma homocysteine and the occurrence of Alzheimer's disease; elevated homocysteine plasma levels has also been established as an independent, graded risk factor for cardiovascular disease. Other diseases, conditions or disorders associated with elevated plasma homocysteine include, but are not limited to, atherosclerosis; neurodegenerative disorders, such as Parkinson's disease; cerebrovascular disorders (i.e., disorders pertaining to blood vessels in the brain), such as stroke; neuropsychiatric disorders, such as bipolar disorder and schizophrenia; diabetes (type II), and arthritis. See, e.g., U.S. Pat. Nos. 5,043,268; 7,794,965; 7,923,041; 8,221,804; and 9,486,441.

Extraction, Manufacturing and Formulation

Seed color and color consistency are important for commercial chia production. The color and mixtures of multiple seed colors (e.g., black, brown, mottled, or white) affects the final color of the product and can lead to color inconsistency among harvests. This is particularly important when the seed oil is used for cosmetics. Uniform seed color is desirable and white seeds are preferable because the oil has a lighter color. Heretofore, efforts to obtain compositions having uniform color have focused on breeding of the chia plants rather than the extraction, manufacturing and formulation processes.

Notably, after extraction and final formulation, the chia compositions may undergo color change, and the color may change and darken over time due to degradation. Prior art methods have not addressed the problems of stability and color change over time. Furthermore, the prior art has not recognized the importance of PP2A modulation as a property for chia-containing products. Accordingly, the prior art methods do not optimize for inhibiting PP1A demethylation activity. In summary, prior art extraction, manufacturing and formulation methods relating to chia compositions and products do not address the issues of optimizing for inhibiting PP2A demethylation activity, color consistency and stability. See, e.g., U.S. Pat. Nos. 5,445,822; 6,117,476; 6,156,369; 6,827,965; 7,955,627; 8,409,636; 8,460,727; 8,252,354; 9,386,795; 9,532,587. Clearly, improved methods and compositions are needed.

BRIEF SUMMARY OF THE INVENTION

One embodiment of the presently disclosed subject matter provides a method of preparing a composition from chia seeds that includes introducing a first solvent to chia seeds to form a mixture, agitating the mixture at a maintained temperature for a period of time above room temperature, filtering the chia seeds from the mixture, evaporating the mixture under reduced pressure to remove the first solvent (e.g., evaporating under reduced pressure with a rotary evaporator) to form a crude chia seed oil. The present method further includes introducing a second solvent to the crude chia seed oil to form a solution, adding a decolorant to the solution, agitating the solution containing the decolorant for a second period of time, filtering the decolorant from the solution and evaporating the second solvent from the solution under reduced pressure to prepare the composition. In one embodiment, the method further includes grinding the chia seeds prior to introducing the first solvent.

In one embodiment the first solvent is an ionic liquid. In one embodiment, the first solvent is a polar solvent, such as a polar probe solvent or a polar aprotic solvent. In one exemplary embodiment the first solvent is selected from acetonitrile, methanol, ethyl acetate, carbon disulfide, dichloromethane, trichloromethane, carbon tetrachloride, nitromethane, glyoxal, formic acid, supercritical carbon dioxide and tetramethylethane; or alternatively selected from acetonitrile, ethyl acetate, dichloromethane, glyoxal, supercritical carbon dioxide and tetramethylethane. In one embodiment, the first solvent is acetonitrile. According to exemplary embodiments, the ratio of the first solvent to chia seed is from about 2:1 to about 4:1 (w/v) (e.g., 3:1 w/v).

In another embodiment, the mixture containing the first solvent is agitated for least 12 hours and/or the maintained temperature is at least 40° C. In certain embodiments, the mixture is evaporated under reduced pressure with a rotary evaporator to form the crude chia seed oil.

In yet another embodiment, the second solvent is easily removable using vacuum evaporation at room temperature. For example, the second solvent can have a boiling point of less than 110° C., or less than 85° C. at 1 atm pressure and/or a boiling point under vacuum (e.g., at or below 40 mmHg) of less than 45° C. In one embodiment, the second solvent is selected from methyl t-butyl ether, dichloromethane, ethyl acetate, heptane, and ethanol (e.g., methyl t-butyl ether).

In a further embodiment, the decolorant is an absorbent, such as an absorbent is selected from activated carbon, silica gel, decolorizing clay and activated alumina. In certain embodiments, the absorbent is Fuller's earth. In another embodiment, the absorbent is activated carbon. In one embodiment, the solution is agitated with the decolorant for at least 8 hours and/or filtered from the solution. The solution can be filtered from the solution rising two filers (e.g., serially). In one embodiment at least one of the filters is diatomaceous earth and/or a silica gel filter.

Another embodiment of the presently disclosed subject matter provides a method of preparing a composition from chia seeds that includes introducing a first polar protic solvent to chia seeds to form a mixture, agitating the mixture at a maintained temperature for a period of time above room temperature, filtering the chia seeds from the mixture, evaporating the mixture under reduced pressure to remove the first solvent and to form a crude chia seed oil, introducing a second solvent to the crude chia seed oil to form a solution, heating the solution to an elevated temperature for a second period of time, gradually cooling the solution to below room temperature for a third period of time, and then heating the solution to about 15-25° C. for a fourth period of time; and evaporating solvent from the solution under reduced pressure to prepare the composition.

In one embodiment, the method further includes adding a decolorant to the solution, agitating the solution containing the decolorant, and filtering the decolorant from the solution. In one embodiment, the decolorant is activated carbon.

In another embodiment, the first solvent and/or the second solvent is independently selected from ethanol, butanol, 2-ethylhexanol, isobutanol, isopropanol, methanol, propanol, glycerol and propylene glycol. For example, in one embodiment, the first solvent and/or the second solvent is independently selected from ethanol, butanol, 2-ethythexanol, isobutanol, isopropanol, and propanol. In one embodiment, the first solvent and the second solvent are ethanol (e.g., ethanol is in aqueous solution and present in time solution in an amount from about 70% to about 90% (v/v)).

In yet another embodiment, the mixture is agitated for at least 12 hours and the maintained temperature is at least 40° C. and/or the mixture is evaporated under reduced pressure with a rotary evaporator.

One embodiment of the presently disclosed subject matter provides a method of enriching the free acid content in chia seed oil. The method includes obtaining an initial chia seed oil composition, introducing an alcohol to the initial chia seed oil composition in the presence of a base for a period of time to form a mixture, introducing an acid to the mixture after the period of time, and removing an aqueous layer from the mixture to obtain the chia seed oil with enriched free acid content. The initial chia seed oil composition can be commercially obtained or synthesized according to any one of the methods disclosed herein.

In one embodiment, the alcohol that is introduced to the initial chia seed oil is a lower alcohol. In one embodiment, the base is a strong base. In one embodiment, the acid is a strong acid. In one embodiment, the alcohol is selected from methanol and ethanol and/or the base is selected from sodium hydroxide and potassium hydroxide. The period of time that the alcohol and base are in contact with the initial chia seed oil composition can range, in exemplary embodiments, from about 12 hours to about 24 hours (e.g., 18 hours), during which time the mixture can be agitated or stirred at, for example, room temperature. The alcohol can, in exemplary embodiments, be selected from methanol and ethanol and/or the acid can be, for example, hydrochloric acid.

The method of enriching the free acid content of chia can be employed to provide enriched free acid compositions that can be mixed with un-enriched compositions to improve stability. Accordingly, one embodiment of the presently disclosed subject matter provides a method of preparing a chia seed oil enriched in free acid, that includes obtaining as initial chia seed oil composition and separating a portion thereof for enrichment, and preparing an enriched free acid portion. The enriched free acid portion process includes introducing an alcohol (e.g., a lower alcohol) to the portion of the chia seed oil composition for enrichment in the presence of a base (e.g., a strong base) for a period of time to form a mixture, introducing an acid (e.g., a strong acid) after the period of time to the mixture, removing an aqueous layer from the mixture to prepare the enriched free acid portion. The method further includes adding a first amount of the enriched free acid portion to a second amount of the initial chia seed oil composition, and washing the combined chia seed oil with an aqueous solvent and drying the combined chia seed oil.

In certain embodiments, the weight ratio of the first amount second amount (i.e., the ratio of the enriched composition:unenriched composition) is from about 0.5 to 2.0 (e.g., 1.0). The aqueous solvent can be, for example, water. The combined chia oil can be dried by introduction to a drying agent, such as, for example, anhydrous magnesium sulfate and anhydrous sodium sulfate.

Any one of the above disclosed embodiments can further include, in certain further embodiments, analyzing a sample of the composition for an amount of cis,cis,cis-9,12,15-octacedatriencoic acid (ALA) and/or an amount of cis,cis-9,12-octadecadienoic acid (LA). The method can further include rejecting the composition if the amount of cis,cis,cis-9,12,15-octacedatriencoic acid (ALA) is below 12 wt % and/or the amount of cis,cis-9,12-octadecadienoic acid (LA) is below 2 wt % or 1.6 wt %. The amount (free levels) of ALA and/or LA can be increased, in exemplary embodiments, by the enrichment process described herein.

A composition (e.g., a pharmaceutical composition) can be prepared by the process of any one of the above disclosed embodiments. For example, the composition can be provided as a unit dosage suitable for administration to a human subject.

Another embodiment of the presently disclosed subject matter provides a composition that includes an extract of chia seeds, in which the amount of cis,cis,cis-9,12,15-octacedatriencoic acid (ALA) is at least 4 $\mu$g/mL or at least 8 $\mu$g/mL, and/or the amount of cis,cis-9,12-octadecadienoic acid (LA) is at least 0.5 $\mu$g/mL or at least 1 $\mu$g/mL.

Another embodiment of the presently disclosed subject matter provides a method of treating a neurodegenerative disease in a subject that includes administering to the subject a composition comprising an extract of chia seeds. In one embodiment, the neurodegenerative disease is selected from Alzheimer's Disease and Parkinson's Disease, and/or the subject exhibits, or is at risk for exhibiting, Tau hyper-phosphorylation, and/or the subject exhibits, or is at risk for exhibiting, $\alpha$-synuclein hyper-phosphorylation, and/or the subject exhibits, or is at risk for exhibiting, abnormally elevated homocysteine levels. In one embodiment, the chia seed composition is orally administered as a pill, tablet, capsule, syrup or a drink or other pharmaceutically acceptable oral dosage form.

Yet another embodiment of the presently disclosed subject matter provides a method of treating a skin disorder, medical condition or disease in a subject comprising administering to the subject a composition comprising an extract of chia seeds. Far example, in one embodiment, the skin disorder, medical condition or disease is selected from rosacea, atopic dermatitis, seborrheic dermatitis, and psoriasis. In one embodiment, acne is treated by administering an extract of chia seeds. The chia seed composition can be topically administered as a cream, lotion, cleanser, ointment or other pharmaceutically acceptable topical dosage form.

Another embodiment of the presently disclosed subject matter provides a method of inhibiting bacterial growth on a surface comprising applying to the surface a composition comprising an extract of chia seeds. In one embodiment, the growth of *Cutibacterium acnes* and/or *Staphylococcus aureus* is inhibited. The surface can be skin, and the chia seed composition can be topically administered as a cream, lotion, cleanser, ointment or other pharmaceutically acceptable topical dosage form. In another embodiment, the surface is a household surface, such as a kitchen surface or a bathroom surface.

The above-described methods can be employed via administering a chia seed composition prepared by any one of synthesis methods described herein.

Another embodiment of the presently disclosed subject matter provides a method of selecting a chia seed plant variety for use in preparing chia seed compositions. The method includes assaying said compositions for inhibition of a PP2A demethylation activity by a PP2A dernethylating enzyme. In one embodiment, the PP2A demethylating enzyme is PME-1 methylesterase.

In certain embodiments, this assaying includes determining a half maximal inhibitory concentration ($IC_{50}$) against PP2A demethylation by the demethylating enzyme. In certain embodiments, the method further includes selecting the chia seed plant variety for use when the determined half maximal inhibitory concentration ($IC_{50}$) is 30 $\mu$g/mL or below.

Another embodiment of the presently disclosed subject matter provides a method of selecting a chia seed plant variety for use in preparing chia seed compositions that includes assaying the compositions for cis,cis,cis-9,12,15-octacedatriencoic acid (ALA) and cis,cis-9,12-octadecadienoic acid (LA) concentrations. In certain embodiments, the method further includers selecting the chia seed plant variety for use when the assayed cis,cis,cis-9,12,15-octacedatriencoic acid (ALA) concentration is at least 8 $\mu$g/mL. In another embodiment, the method further includes selecting the chia seed plant variety for use when the assayed cis,cis-9,12-octadecadienoic acid (LA) concentration in the composition is less than 0.5 $\mu$g/mL. In another embodiment, the method further includers selecting the chia seed plant variety for use when the assayed cis,cis,cis-9,12,15-octacedatriencoic acid (ALA) concentration is at least 4 $\mu$g/mL and the assayed cis,cis-9,12-octadecadienoic acid (LA) concentration is at least 0.5 $\mu$g/mL, or at least 1 $\mu$g/mL.

Another embodiment of the presently disclosed subject matter provides a sunscreen product that includes a chia seed extract. The sunscreen product can include a composition prepared, or a composition described, by any one of the presently disclosed embodiments. Methods of protecting against UV radiation comprising topically administering compositions obtained from chia seeds are also provided.

Any one of the above-described extracts, and compositions containing these extracts, can be, in certain embodiments, topically administered, such as, for example, as a cream, lotion, cleanser, ointment or other pharmaceutically acceptable topical dosage form. Alternatively, any one of the above-described extracts, and compositions containing these extracts, can be, in certain embodiments, orally administered, such as, for example, as a pill, tablet, capsule, syrup or a drink or other pharmaceutically acceptable oral dosage form. In either topical or oral form, the extract can be administered together with other botanicals and vitamins.

The invention is further directed to the general and specific embodiments defined, respectively, by the claims appended hereto, which are incorporated by reference herein.

BRIEF DESCRIPTION OF THE DRAWINGS

The following detailed description of exemplary embodiments of the subject disclosure will be better understood when read in conjunction with the appended drawings. For the purpose of illustrating the present disclosure, exemplary embodiments and data from exemplary embodiments are shown in the drawings. It should be understood, however, that the subject application is not limited to the precise arrangements and instrumentalities shown.

DETAILED DESCRIPTION OF THE INVENTION

Figure 1:
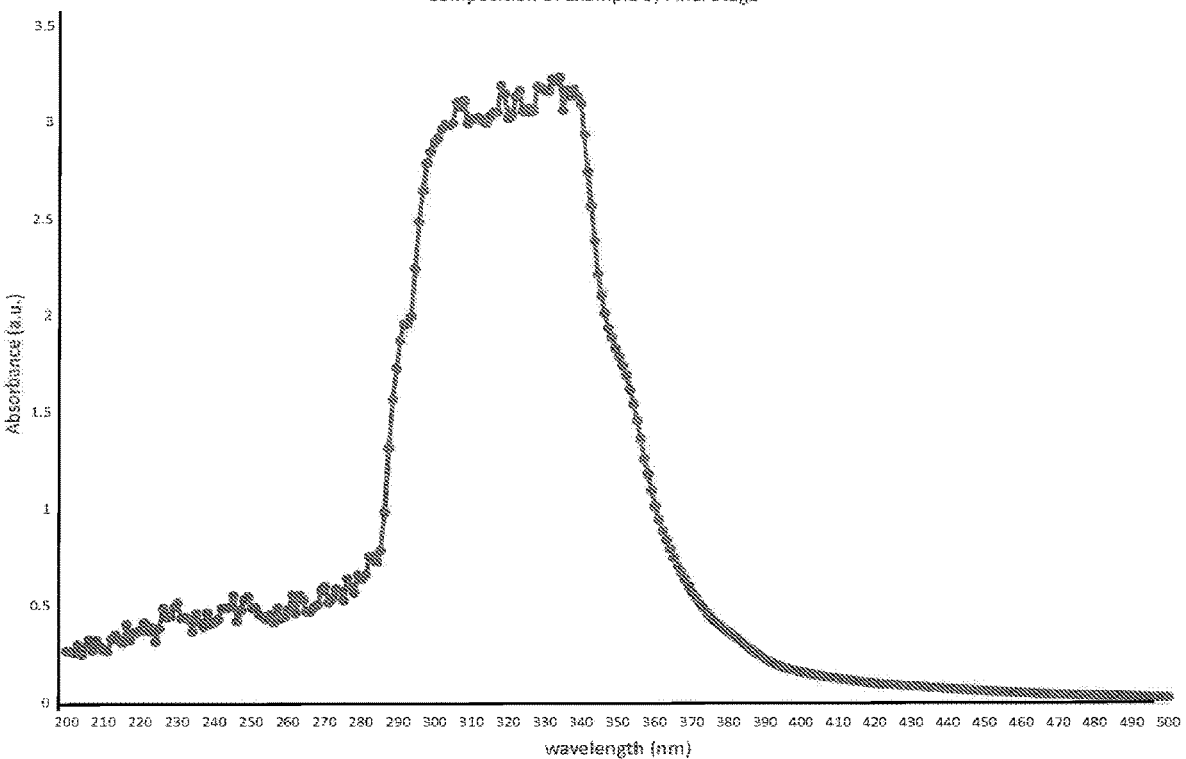
FIG. 1 is a plot of the absorbance (y-axis) at various wavelengths of light (x-axis) of the Final Stage Product of Example 9, as described in Example 11.

The invention can be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

Terms And Definitions

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated.

To provide a more concise description, some of the quantitative expressions given are not qualified with the term "about." It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," and "the" are to be understood as meaning both singular and plural, unless explicitly stated otherwise, Thus, "a," "an," and "the" (and grammatical variations thereof where appropriate) refer to one or more.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. Thus, the term "example" is used to provide exemplary instances of the item in discussion, not an exhaustive or limiting list thereof. Similarly, adjectives such as "conventional," "traditional," "normal," "criterion," "known," and terms of similar meaning should not be construed as limiting the item described to a given time period or to an item available as of a given time, but they should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

The term "composition" is intended to encompass a product including the herein described extracts and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. In certain embodiments, a "composition," as used herein, is pharmaceutically acceptable and suitable for oral administration. In alternative embodiments, a "composition," as used herein, is pharmaceutically acceptable and suitable for topical administration.

The term "carrier" refers to an adjuvant, vehicle, or excipients, with which the compound is administered. In certain embodiments of this invention, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The active extract is generally administered as part of a formulation that includes nonmedical agents. The dosage form has unique physical and pharmaceutical characteristics. Dosage forms, for example, can be solid, liquid, gel or gaseous. "Dosage forms" can include for example, a capsule, tablet, caplet, gel caplet (gelcap), syrup, a liquid composition, a powder, a concentrated powder, a concentrated powder admixed with a liquid or topical gel or lotion, a chewable form, a swallowable form, a dissolvable form, an effervescent, a granulated form, a topical form and an oral liquid solution. In a specific embodiment, the dosage form is a solid dosage form, and more specifically, comprises a tablet or capsule. In another specific embodiment, the dosage form is a topical dosage form, and more specifically, comprises a gel, lotion or other form suitable for application to human skin.

The term "pharmaceutically acceptable," as used in connection with compositions of the invention, refers to molecular entities and other ingredients of such compositions that are physiologically tolerable and do not typically produce untoward reactions whets administered to an animal (e.g., human) according to their intended mode of administration (e.g., oral or topical).

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" or "suitable for topical administration" refers to a sterile, pharmaceutical product produced under good manufacturing practices (GMP). The term "suitable for oral administration" or "suitable for topical administration" can, when specified, also mean approved by a regulatory agency of the Federal or a state government or listed in the U.S. Pharmacopeia or other generally recognized pharmacopeia for use in animals (e.g. mammals), and more particularly in humans.

As used herein, the term "disorder" is used interchangeably with "disease" or "condition". For example, a neurological disorder also means a neurological disease or a neurological condition.

The terms "treat," "treating," and "treatment" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. These terms also include ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound is administered to a subject (e.g. a mammal). The "effective amount" will vary, depending on the compound, the disease (and its severity), the treatment desired, age and weight of the subject, etc.

As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

As used herein, the term "modulate" refers to change in a parameter (e.g., a change in a binding interaction or an activity, etc.). Modulation can refer to an increase or a decrease in the parameter (e.g., an increase or decrease in binding, an increase or decrease in activity, etc.).

As used herein, the term "modulator" refers to an agent that alters level and/or activity of its target (e.g., in the GPCR signal transduction pathway). In some embodiments, a modulator alters interaction between a protein in the GPCR signal transduction pathway and one or more other entities. In some embodiments, a modulator alters interaction between a modulator alters interaction between a protein in the GPCR signal transduction pathway and a substrate. Determination of whether an agent is a modulator can be performed directly or indirectly. Determination of whether an agent modulates an interaction can be performed directly, e.g., using an assay that detects the interaction between a protein in the GPCR signal transduction pathway and a substrate. Determination of whether an agent modulates an interaction can be performed with a technique that indirectly detects modulation, e.g., a technique that detects a biological activity that is downstream of, and dependent on, the protein-substrate interaction.

The terms "individual," "subject," and "patient" are used interchangeably herein and can be a vertebrate, in particular, a mammal, more particularly, a primate (including non-human primates and humans) and include a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, the term "antioxidant" is a substance that protects cells from free radicals, which are highly reactive chemicals often containing oxygen atoms, that are capable of damaging important cellular components, such as DNA and lipids.

As used herein, the term "chia" shall refer to *Salvia hispanica.*

As used herein, the term "cognitive function" refers to the ability to perform mental tasks, such as thinking, learning, judging, remembering, computing, controlling motor functions, and the like. The expression "resilience of cognitive function" refers to the ability of functional elements of cognitive function to resist deterioration over time. As used herein, the term "cognitive function enhancing amount" refers to that amount of the composition of the present invention that will noticeably impact the ability to perform mental tasks, as measured by tests for memory, computation, attention, or other mental or cognitive attribute, or as suggested by an individual's perception of his or her abilities in these realms.

As used herein, the term "comestible" refers to a material that is suitable for human consumption, including a material that can be ingested by oral and by a non-oral means, e.g., an inhalant or a snuff. For purposes of the present invention, the term includes supplemented or enhanced foods.

As used herein, the term "cosmeceutical" refers to a cosmetic product that contains a biologically active compound that is thought to have pharmaceutical or medicinal effects. Examples of such an effect would include "anti-aging," "antipollution" and reduction or prevention of inflammation.

The term "cosmetic" refers to a treatment or product intended to restore or improve a person's appearance.

The terms "dietary supplement" and "nutritional supplement" are used interchangeably herein to mean (1) a product intended to supplement the diet that bears or contains one or more of the following dietary ingredients: a vitamin, a mineral, an herb or other botanical, an amino acid, a dietary substance for use by man to supplement the diet by increasing the total dietary intake; or a concentrate, metabolite, constituent, extract, or combination of any ingredient described above; and (2) a product that (i) is intended for ingestion; (ii) is not represented for use as a conventional food or as a sole item of a meal or the diet; and (iii) is labeled as a dietary supplement.

The term "health" or "healthy" as used herein refers to a general condition of the body or mind with reference to soundness and vigor, as well as freedom from disease or ailment.

The term "partitioning" as used herein refers to a process that takes advantage of the differential solubility of a substance in two solvents.

The terms "soluble" and "solubility" refer to the property of being susceptible to being dissolved in a specified fluid (solvent). The term "insoluble," as used herein refers to the property of a material that has minimal or limited solubility in a specified solvent.

The term "solvent" as used herein refers to a substance, usually liquid, capable of dissolving or dispersing one or more other substances. Chemists have classified solvents into two broad categories according to their polarity: polar and nonpolar. A common measure of the polarity of a solvent is the dielectric constant. The term "polar solvent" as used herein refers to a compound that is composed of polar molecules. A "polar molecule" is one in which there is some separation of charge in the chemical bonds, so that one part of the molecule has a slight positive charge and the other a slight negative charge. Polar solvents can be further classified as prone or aprotic. The term "protic" refers to a hydrogen atom attached to an electronegative atom, while the term "aprotic" refers to a molecule that does not contain an O—H bond. A "polar protic solvent" can be represented by the general formula ROH; the polarity of the polar protic solvent stems from the bond dipole of the O—H bond. Examples of polar protic solvents include, but are not limited to, water, alcohols, and acetic acid. A "dipolar aprotic solvent" is one that contains a bond that has a large bond dipole. Typically, this bond is a multiple bond between carbon and either oxygen or nitrogen. Most dipolar aprotic solvents contain a C—O double bond. Examples of dipolar aprotic solvents include, but are not limited to, acetone and ethyl acetate. As the number of groups —CH$_2$— in ROH increases, and the relative amount of hydrocarbon character increases, the polarity decreases. The term "nonpolar solvent" refers to compounds that have low dielectric constants and are not miscible with water. Examples of nonpolar solvents include, but are not limited to, benzene, carbon tetrachloride, and hexanes.

The term "lower alcohol" as used herein refers to short-chain alcohols having less than 10 carbon atoms and includes, for example, methanol, ethanol, propanol, butanol, isopropanol, tert-butanol, octanol, and derivatives (e.g., branched derivatives) of each of the above.

The term "strong acid" as used herein refers to an acid that completely dissociates in water to yield H+ and the conjugate base, as understood by those of ordinary skill in the chemical arts. Strong acids include chloric acid, hydrobromic acid, hydrochloric acid, hydroiodic acid, nitric acid, perchloric acid and sulfuric acid.

The term "strong base" as used herein refers to a base that that can remove a proton (H+) from (or deprotonate) a molecule of even a very weak acid (such as water) in an acid-base reaction, as understood by those of ordinary skill in the chemical arts. Strong bases include hydroxides of alkali metals and alkaline earth metals, like NaOH and Ca(OH)$_2$.

The term "well-being" as used herein refers to a subject's physical and mental soundness.

A composition of the present invention, alone or in combination with other active ingredients, can be administered to a subject in a single dose or multiple doses over a period of time, generally by oral or topical administration. As used herein, the terms "therapeutically effective amount," "memory-enhancing amount", and "cognition enhancing amount" refer to the amount of the composition of the invention that results in a therapeutic or beneficial effect, including a subject's perception of health or general well-being, following its administration to a subject.

it is believed that an increase in the level of PP2A methylation, or PP2A modulation in general, will bring about the protection or enhancement of cognitive functioning, or preventing a cognitive disorder from manifesting or deepening. Thus, the therapeutic effect of the compositions of the present invention can exert a protective or enhancing effect on cognitive function; minimize, prevent or ameliorate cognitive symptoms of a disease or disorder, or can have any other beneficial or desired effects and/or therapeutic results.

The concentration of the substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose.

A skilled artisan can determine a therapeutically effective amount of the inventive compositions by determining the unit dose. As used herein, a "unit dose" refers to the amount of inventive composition required to produce a response of 50% of maximal effect (i.e. $ED_{50}$). The unit dose can be assessed by extrapolating from dose-response curves derived from in vitro or animal model test systems. The amount of compounds in the compositions of the present invention which will be effective in the treatment of a particular disorder or condition will depend on the nature of the disorder or condition, and can be determined by standard clinical techniques. (See, for example, Goodman and Gilman's The Pharmacological Basis of Therapeutics, Joel G. Harman, Lee E. Limbird, Eds.; McGraw Hill, New York, 2001; The Physician's Desk Reference, Medical Economics Company, Inc., Oradell, N.J., 1995; and Drug Facts and Comparisons, Facts and Comparisons, Inc., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the cognitive function enhancing amount of the compositions of the present invention is administered one or more times per day on a regular basis. A typical dose administered to a human is between about 1 mg and about 10 g of the composition, preferably between 1 mg and 1 g of the composition.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment where it is desirable to substantially increase methylated PP2A, it is preferred that the therapeutic dosage be close to the maximum tolerated dose. For chronic preventive use, lower dosages may be desirable because of concerns about long term effects. However, the instant compositions are commonly believed to be safe and have a history of human use. Alternatively, the composition of the present invention can be administered at least once per day in combination with a prescribed drug. For example, the composition of the present invention can be administered together with existing anti-cholinesterase drugs now prescribed for Alzheimer's, with various anti-inflammatory agents, or with statins.

Reference will now be made to the embodiments of the present invention, examples of which are illustrated by and described in conjunction with the accompanying examples. While certain embodiments are described herein, it is understood that the described embodiments are not intended to limit the scope of the invention. On the contrary, the present disclosure is intended to cover alternatives, modifications, and equivalents that can be included within the invention as defined by the appended numbered embodiments.

In another aspect, the compositions of the present invention are administered in combination with a dietary or nutritional supplement believed to have beneficial health effects. Examples of such supplements include: Coenzyme Q10 (also known as CoQ10, Q10, vitamin Q10, ubiquinone and ubidecarenone); idebenone; huperzine A; galantamine; vincamine; vinpocetine (a semisynthetic derivative of vincamine); ccetyl-L-carnitine (an acetylated derivative of carnitine); dehydroepiandrosterone (DHEA); phosphatidylcholine; gingko; ginseng; vitamin E (DL-alpha-tocopherol) and it tocol and tocotrienol derivatives exhibiting qualitatively the biological activity of alpha-tocopherol; N-acetyl-cysteine (NAC); B vitamins, such as folic acid; lecithin; choline (trimethyl ethanolamine); fish oil; and L-deprenyl (selegiline, Eldepryl®).

The compositions of the invention can be used alone or in combination with other pharmaceuticals or herbals to prolong mental health, to maintain or enhance cognitive functioning or memory, or to preserve mental or physical well-being and health. The compositions can also be used to prevent or treat effects a number of ailments, including, but not limited Alzheimer's disease; Parkinson's disease; heart disease; arthritis; age-related degeneration, functional impairments, and diseases; diabetes, and cancer, have on cognitive function.

The effectiveness of the compositions and methods of the present invention can be assayed by a variety of protocols. The effects of increasing cognitive function in a human subject can be determined by methods routine to those skilled in the art including, but not limited to, both paper and pencil, and computer tests. One of skill in the art can also directly measure PP2A methylation levels, tau protein phosphorylation levels, neurofibrillary tangle formation and neurodegeneration in animal models.

Another aspect of the present invention provides a method for inhibiting demethylation of PP2A by PME-1 methylesterase comprising administering to a subject in need thereof an effective amount of a chia seed composition. Subjects that are in need of inhibition of demethylation of PP2A by PME-1 methylesterase, and hence can be administered the presently disclosed extracts or compositions, include, but are not limited to, subjects that exhibit, or are at risk for exhibiting, Tau hyper-phosphorylation, α-synuclein hyper-phosphorylation, and/or abnormally elevated homocysteine levels. For example, the presently disclosed compositions can be administered to subjects who exhibit abnormal one carbon metabolism (e.g., subjects who have disruptions in folate, methionine and choline pathways).

According to another embodiment, the composition inhibits a demethylating activity of a demethylating enzyme that acts on a protein phosphatase 2A enzyme and thereby stimulates methylation of the protein phosphatase 2A enzyme. According to another embodiment, the composition inhibits at least about 50% of the demethylating activity of the demethylating enzyme. According to another embodiment, the demethylating enzyme is a protein phosphatase 2A specific protein methylesterase. According to another embodiment, the demethylating activity of the protein phosphatase 2A specific protein methylesterase is determined by measuring levels of protein phosphatase 2A methyl esterification.

In one embodiment, the subject in need of the presently disclosed extracts and compositions have been diagnosed with, or is at risk for developing, Alzheimer's Disease. In another embodiment, the subject in need of the presently disclosed extracts and compositions have been diagnosed with, or is at risk for developing, Parkinson's Disease.

In one embodiment, the subject is a healthy subject. For example, the healthy subject may desire to prevent cognitive and/or motor function decline, or they may wish to improve upon their present cognitive and motor function.

The invention also provides methods of enhancing memory in a human, which method includes administering a memory enhancing amount of a presently described composition (e.g., a pill, topical administration or comestible). Methods of enhancing cognitive function in a human, the method comprising the step of administering a cognitive function enhancing amount of a presently described composition, wherein the composition inhibits at least 50% of the demethylating activity of the demethylating enzyme as measured by levels of PP2A methyl esterification.

According to the present invention, the compositions can be used in methods of treating or preventing any disease, condition or disorder where defects in methylation metabolism appear to play a role as evidenced by an association of the disease, condition or disorder with plasma homocysteine levels that are elevated relative to normal plasma homocysteine levels. Such diseases, conditions or disorders include, but are not limited to, neurodegenerative diseases, disorders or conditions, such as Parkinson's disease, neuropsychiatric diseases, disorders or conditions, such as bipolar disorder, Alzheimer's disease, heart disease, arthritis, diabetes and certain cancers. The term "neurodegenerative disease" as used herein refers to a disease, condition or disorder marked by the loss or diminution of an original nerve cell function, and the term "neuropsychiatric" relates to organic and functional diseases, conditions or disorders of the nervous system.

According to yet another embodiment, the compositions can be used in methods of treating or preventing sleep disorders. Sleep disorders that can be treated using the compositions of the present invention include, but are not limited to, insomnia, narcolepsy, familial advanced sleep-phase syndrome (FASPS) and disruption to the circadian rhythm (e.g., jet lag).

According to another embodiment of the present invention, the compositions can be used in methods of treating or preventing eye and vision disorders.

According to yet another embodiment, the compositions of the present invention can be used in methods of treating or preventing a mental disorder. For example, the presently disclosed compositions can be administered to subjects who exhibit abnormal one carbon metabolism (e.g., subjects who have disruptions in folate, methionine and choline pathways). The term "mental disorder" refers to diseases characterized as mood disorders, psychotic disorders, anxiety disorders, childhood disorders, eating disorders, personality disorders, adjustment disorder, autistic disorder, delirium, dementia, multi-infarct dementia and Tourette's disorder in the DSM-IV classification (Diagnosis and Statistical Manual of Mental Disorders, Fourth Edition, American Psychiatric Association, Washington D.C., 1994). In one particular embodiment, the compositions of the present invention are used to treat an autistic disorder.

According to yet another embodiment, the present compositions can be used in methods of treating a traumatic brain injury (TBI).

According to yet another embodiment, the present compositions can be used in methods of treating or preventing a cardiovascular disease or disorder. Cardiovascular diseases and disorders that can be treated using the compositions of the present invention include, but are not limited to, ischemic heart disease, non-ischemic heart disease, myocardial infarction, tachy-pacing induced non-ischemic heart disease, heart failure, atherosclerosis, ischemic stroke, problems with heart valves, and catecholaminergic-induced arrhythmia and symptoms thereof in a subject.

According to yet another embodiment, the present compositions can be used in methods of treating or preventing a metabolic disease or disorder. Metabolic diseases and disorders that can be treated using the compositions of the present invention include, but are not limited to, metabolic syndrome, insulin resistance, glucose intolerance, hyperglycemia, type I diabetes, type II diabetes, hyperlipidemia, hypertriglyceridemia, hypercholesterolemia, dyslipidemia, and polycystic ovary syndrome (PCOS), and symptoms thereof, in a subject.

According to yet another embodiment of the present invention, a pharmaceutical preparation for promoting general health and well-being in a mammalian subject, including a human, is provided that includes a cognitive function-enhancing amount of a composition of the present invention and a pharmaceutically acceptable carrier.

In another embodiment, the subject exhibits, or is at risk for exhibiting, a skin disorder, medical condition or disease. In one embodiment, the subject desires to maintain healthy skin and prevent skin aging.

Another aspect of the present invention provides a method for inhibiting inflammation in a subject comprising administering to a subject an effective amount of a chia seed extract.

In certain embodiments, the present invention provides methods of inhibiting inflammation, and uses of provided extracts and/or compositions in the treatment of inflammation. In certain embodiments, the present invention provides uses of provided extracts and/or compositions in the treatment of diseases that can benefit from edema inhibition, erythema inhibition and/or MPO inhibition, such as treating or lessening the severity of inflammatory diseases or disorders including, but not limited to, inflammation (acute or chronic), asthma, autoimmune diseases, and chronic obstructive pulmonary disease (COPD) (e.g., emphysema, chronic bronchitis and small airways disease, (etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), and central nervous system disorders (e.g., Parkinson's disease).

The present invention also relates to treating or lessening the severity of inflammatory diseases or disorders selected from inflammation (acute or chronic), inflammatory diseases or disorders (e.g., asthma, autoimmune diseases, and COPD including emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), and Parkinson's disease, wherein the method comprises administering to a patient in need thereof a composition of the present invention.

In certain embodiments, the provided compositions of the present invention are capable of effectively inhibiting inflammatory responses. Thus, provided compositions are inhibitors of edema, erythema and myeloperoxidase and are therefore useful for treating one or more disorders associated with inflammatory diseases or disorders as described herein. In particular, the present invention encompasses the finding that certain compositions having superior in vivo activity than other compositions in the same class. Therefore, such compositions are administered to a subject suffering from or susceptible to one or more inflammatory diseases or disorders.

In certain embodiments, the treatment of inflammatory diseases or disorders is achieved using compositions without having the side effects of corticosteroids or NSAIDS.

In certain embodiments, such compositions are administered in vitro. In certain embodiments such compositions are administered in vivo.

Another aspect of the present invention is directed to methods of treating, preventing, or ameliorating inflammation by administering an effective amount of a provided composition.

In some embodiments, one or more inventive compositions, alone or together with one or more other pharmaceutically active agents, is used to whiten skin. In some such embodiments, the composition is applied topically.

In general, the actual quantity of provided compositions of the invention administered to a patient will vary depending on the severity and type of indication, the mode of administration, the particular composition used, the formulation used, and the response desired.

The dosage for treatment is administration, by any of the foregoing means or any other means known in the art, of an amount sufficient to bring about the desired therapeutic effect. Thus, an effective amount includes an amount of a provided composition (or mixture of provided compositions) or pharmaceutical composition of this invention that is sufficient to induce a desired effect, including specifically an anti-inflammation effect.

In general, the provided compositions of the present invention are highly active. Far example, a provided composition can be administered at about 10 µg/kg to about 50 mg/kg body weight, depending on the specific provided composition selected, the desired therapeutic response, the route of administration, the formulation and other factors known to those of skill in the art.

In one embodiment, the compositions to be administered to subjects as described herein, may further comprise botanical extracts obtained from at least one fruit source selected from the group consisting of: juniper berry, schisandra, and strawberry. In another embodiment, the botanical extract is obtained from at least one seed source (e.g., avocado, black raspberry, blueberry, celery, cranberry, fennel, grape, guarana and red raspberry). In one particular embodiment, the seed source is selected from grape, guarana and red raspberry. In another embodiment, the botanical extract is obtained from a least one root, bark or leaf source (e.g., maca root, goldenseal root, turmeric root, magnolia bark, pygeum bark, red raspberry leaf). In a still further embodiment, the root, bark or leaf source is turmeric root. In another embodiment, the botanical extract is obtained from at least one natural source selected from the group consisting of: almond, cocoa powder, Echinacea angustifolia, prickly pear cactus and walnut. In one particular embodiment, the natural source is prickly pear cactus.

The compositions of the present invention can be in a form suitable for oral use, for example, as tablets, troches, lozenges, aqueous or oily suspensions, solutions, dispersible powders or granules, emulsions, hard or soft capsules, syrups or elixirs, pastes, gels or the like. Compositions intended for oral use can be prepared according to any known method, and such compositions can contain one or more agents selected from the group consisting of sweetening agents, flavoring agents, coloring agents, and preserving agents in order to provide pharmaceutically elegant and palatable compositions. Tablets or other oral dosage forms can contain the active ingredient(s) in admixture with non-toxic pharmaceutically-acceptable excipients which are suitable for the manufacture of tablets or oral dosage form.

These excipients can be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets or oral dosage forms can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They also can be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

Compositions of the present invention also can be formulated for oral use as hard gelatin capsules, where the active ingredient(s) is (are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention can be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents can be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also can contain one or more coloring agents, one or more flavoring agents, and one or more sweetening agents, such as sucrose or saccharin.

Compositions of the present invention can be formulated as oily suspensions by suspending the active ingredient in a vegetable oil, for example arachis oil, olive oil, sesame oil or coconut oil, or in a mineral oil, such as liquid paraffin. The oily suspensions can contain a thickening agent, for example, beeswax, hard paraffin or cetyl alcohol. Sweetening agents, such as those set forth above, and flavoring agents can be added to provide a palatable oral composition. These compositions can be preserved by the addition of an antioxidant such as ascorbic acid.

Compositions of the present invention can be formulated in the form of dispersible powders and granules suitable for composition of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by time already mentioned above. Additional excipients, or example, sweetening, flavoring and coloring agents also can be present.

The compositions of the invention also can be in the form of oil-in-water emulsions. The oily phase can be a vegetable oil, for example, olive oil or arachis oil, or a mineral oil, for example a liquid paraffin, or a mixture thereof. Suitable emulsifying agents can be naturally-occurring gums, for example, gum acacia or gum tragacanth, naturally occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also can contain sweetening and flavoring agents.

The compositions of the invention also can be formulated as syrups and elixirs. Syrups and elixirs can be formulated with sweetening agents, for example, glycerol, propylene glycol, sorbitol or sucrose. Such formulations also can contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Liquid based oral dosage forms, like their solid counterparts, can, in certain embodiments contain at least 0.1 mg of a provided composition. One skilled in the art will be able to properly formulate a liquid formulation containing an appropriate amount of a provided composition per fluidic ounce, depending on the additive or carrier selected.

Formulations suitable for buccal administration include tablets and lozenges comprising a composition of the present invention in a flavored base, such as sucrose, acacia or tragacanth; and pastilles comprising the composition in an inert base, such as gelatin and glycerin or sucrose and acacia.

For topical administration formulations, any of a variety of creams, ointments, gels, cleansers, lotions and the like can be employed. For most pharmaceutical formulations, nonactive ingredients will constitute the greater part, by weight or volume, of the preparation. For pharmaceutical formulations, it is also contemplated that any of a variety of measured-release, slow-release or time-release formulations and additives can be employed, so that the dosage can be formulated so as to effect delivery of a provided composition over a period of time. For example, gelatin, sodium carboxymethylcellulose and/or other cellulosic excipients can be included to provide time-release or slower-release formulations, especially for administration by subcutaneous and intramuscular injection. Other additives which can be used include petroleum jelly, lanoline, polyethylene glycols, alcohols, transdermal enhancers, and combinations of two or more thereof.

In some embodiments, formulations suitable for topical application achieve transdermal delivery. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical can generally include a backing layer impermeable to the pharmaceutical, a reservoir to house the pharmaceutical, and an adhesive cover to be removed upon use of the patch and for adhesion to the skin of a patient. Formulations suitable for transdermal administration can also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration can also be delivered by iontophoresis (passage of a small electric current (~15 mA) to "inject" electrically charged ions into the skin) through the skin. For this, the dosage form typically takes the form of an optionally buffered aqueous solution of the active composition.

In practical use, a provided composition of the present invention can be combined as the active ingredient in an admixture with a pharmaceutical carrier according to conventional pharmaceutical compounding techniques. The carrier can take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media can be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

According to yet another embodiment of the present invention, a comestible for promoting general health and well-being in a mammalian subject, including a human, including one or more of the compositions described herein. According to another embodiment, the comestible is a beverage. According to another embodiment, the beverage is selected from the group consisting of a drink comprising water, a fruit drink, a coffee, a tea, an energy drink, a baby formula, an adult nutritional drink, a health drink, and a sports drink. According to another embodiment, the comestible is a food. According to another embodiment, the comestible is a cereal. According to another embodiment, the comestible is a chewing gum. According to another embodiment, the comestible is a candy.

In another embodiment, the compositions of this invention can be used in cosmetic or cosmeceutical products, including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. The compositions of this invention can also be used in skincare products, including products for hydration, anti-aging, brightening, cleansing, face glow, line smoothing and acne.

The compositions of the present invention can be incorporated into all types of vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

Additional Ingredients—Cosmetic Ingredients

The CTFA international Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no, 5, D&C orange no. 4, D&C red no. 17, D&C red no. 33, D&C violet no. 2, D&C yellow no. 10, and D&C yellow no. 11), decolorants (e.g., absorbents), lubricants, solvents, moisturizers (including, e.g., emollients, humectants, film formers, occlusive agents, and agents that affect the natural moisturization mechanisms of the skin), water-repellents, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and nonsteroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks, Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bisbenzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (*Prunus armeniaca*) kernel oil, arginine, arginine aspartate, arnica montana extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, calendula officinalis extract, calendula officinalis oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia ternifolia nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*citrus aurantium dulcis*) oil, palm (*Elaeis guineensis*) oil, palmitic acid, pantethine, panthenol, panthenyl ethyl ether, paraffin, PCA, peach (*Prunes persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil. safflower (*Carthamus tinctorius*) oil, sage (*Salvia officinalis*) oil, sandalwood (*Santalum album*) oil, serine, serum protein, sesame (*Sesamum indicum*) oil, sheer butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgar*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non--limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicone containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes), A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicone 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described, for example, in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from 160° C. to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grape-fruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentacrytritol. Carbopol™ 900 series from B.F. Goodrich).

Non-limiting examples of crosslinked polyacrylate polymers include cationic and nonionic polymers. Examples are described in U.S. Pat. Nos. 5,100,660; 4,849,484; 4,835, 206; 4,628,078; and 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of 1-3 linked glucose units with a 1-6 linked glucose every three units.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium, carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

j. pH Adjustor

As is widely recognized in the art, since the pH of the skin is 5.5, compositions for topical skin application (to avoid irritation) should preferably have a pH value of between 4.0 and 9.0, preferably between 5.0 and 8.0, a pH adjusting composition is typically added to bring the pH of the composition to the desired value. The compositions of the present invention therefore preferably are formulated to have a pH value that ranges between about 4.0 and about 9.0, more preferably between about 5.0 and about 8.0.

Suitable pH adjusting agents include, for example, but are not limited to, one or more adipic acids, glycines, citric acids, calcium hydroxides, magnesium aluminometasilicates, buffers or any combinations thereof.

j. Deodorant Agent

As used herein "deodorant agent" refers to a substance for inhibiting or masking perspiration or other bodily odors. Representative examples of deodorant agents that are usable in the context of the present invention include, without limitation, quaternary ammonium compounds such as cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above. Antiperspirant agents can be incorporated in the compositions of the present invention either in a solubilized or a particulate form and include, for example, aluminum or zirconium astringent salts or complexes.

k. Hair Conditioning Agent

Suitable hair conditioning agents that can be used in the context of the present invention include, for example, one or more collagens, cationic surfactants, modified silicones, proteins, keratins, dimethicone polyols, quaternary ammonium compounds, halogenated quaternary ammonium compounds, alkoxylated carboxylic acids, alkoxylated alcohols, alkoxylated amides, sorbitan derivatives, esters, polymeric ethers, glyceryl esters, or any combinations thereof.

l. Chelating Agent

Chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

m. Solubilizing Agent

As used herein "solubilizing agents" are those substances that enable solutes to dissolve. Representative examples of solubilizing agents that are usable in the context of the present invention include, without limitation, complex-forming solubilizers such as citric acid, ethylenediaminetetraacetate, sodium meta-phosphate, succinic acid, urea, cyclodextrin, polyvinylpyrrolidone, diethylammonium-ortho-benzoate, and micelle-forming solubilizers such as TWEEN® and spans, e.g., TWEEN 80®. Other solubilizers that are usable for the compositions of the present invention are, for example, polyoxyethylene sorbitan fatty acid ester, polyoxyethylene n-alkyl ethers, n-alkyl amine n-oxides, polyoxamers, organic solvents, such as acetone, phospholipids and cyclodextrins.

n. Penetration Enhancer

A "penetration enhancer" is an agent known to accelerate the delivery of a substance through the skin. Suitable penetration enhancers usable in the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research incorporated, Richmond, Va.), alcohols, and the like. The permeation enhancer can also be a vegetable oil. Such oils include, for example, safflower oil, cottonseed oil and corn oil.

o. Colorant

Colorants can also be used in the compositions of the invention. Colorants include pigments or dyes or a combination thereof as the cosmetic benefit requires. Preferred pigments include, but are not limited to, iron oxides, and titanium oxides. Suitable dyes include FD&C approved colorants, D&C approved colorants, and those approved for use in Europe and Japan. See Marmion, D. M., Handbook of US Colorants for Food, Drugs, Cosmetics, and Medical Devices, 3rd ed, 1991 herein incorporated by reference.

p. Anti-Fungal Agent

The term "anti-fungal agent" as used herein means any of a group of chemical substances having the capacity to inhibit the growth of or to destroy fungi, Anti-fungal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

q. Antibiotic Agent

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefinetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin: Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

r. Anti-Viral Agent

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscarnet, Indinavir, Interferon-.alpha., interferon-.beta., Interferon-.gamma., Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

s. Anti-Acne Agent

Suitable anti-acne agents of the present invention include, without limitation, keratolytics, such as salicylic acid, sulfur, glycolic, pyruvic acid, resorcinol, and N-acetylcysteine; and retinoids such as retinoic acid and its derivatives (e.g., cis and trans, esters).

t. Steroidal Anti-Inflammatory Agent

"Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

u. Non-Steroidal Anti-Inflammatory Agent

"Non-steroidal anti-inflammatory agents" refers to a large group of agents that are aspirin-like in their action, including ibuprofen (Advil)®, naproxen sodium (Aleve)®, and acetaminophen (Tylenol)®. Additional examples of non-steroidal anti-inflammatory agents that are usable in the context of the present invention include, without limitation, oxicams, such as piroxicam, isoxicam, tenoxicam, sudoxicarn, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, moclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents can also be employed, as well as the dermatologically acceptable salts and esters of these agents. For example, etofenamate, a flufenamic acid derivative, is particularly useful for topical application.

v. Anti-Protozoal Agent

The term "anti-protozoal agent" as used herein means any of a group of chemical substances having the capacity to inhibit the growth of or to destroy protozoans used chiefly in the treatment of protozoal diseases. Examples of antiproto- zoal agents, without limitation include pyrimethamine (Daraprim®) sulfadiazine, and Lencovorin.

w. Antipruritic Agent

"Antipruritic agents" as used herein refers to those substances that reduce, eliminate or prevent itching. Suitable antipruritic agents include, without limitation, pharmaceutically acceptable salts of methdilazine and trimeprazine.

x. Anti-dandruff Agent

"Anti-dandruff agents" as used herein refer to agents that reduce, eliminate or prevent a scurf from forming on skin, especially of the scalp, that comes off in small white or grayish scales. Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imdazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopiroxolamine, and mixtures thereof.

y. Anit-Hyperpigmenting Agent

"Anti-Hypopigmenting agents" refer to substances capable of depigmenting the skin. Suitable anti-hyperpigmenting agents include hydroquinones, mequinol, and various protease inhibitors including serine protease inhibitors, active soy and retinoic acid.

z. Cleansing Agent

Cleansing agents which can be use in the present invention include surfactant-based cleansing agents, examples of which have been listed hereinabove, Other non-surfactant-based cleansing agents known to those of skill in the art can also be employed.

"Caustic agents" refer to substances capable of destroying or eating away epithelial tissue by chemical action. Caustic agents can be used to remove dead skin cells. For example, beta-hydroxy acids, naturally derived acids with a strong kerolytic effect, are useful for problem skin, acne or peeling.

According to an exemplary embodiment, all or a portion of chia seed oil composition can be hydrolyzed to increase the free fatty acid content, including the concentration of ALA and LA, that is not part of a triglyceride. For example, an alcohol can reacted with chia seed oil composition in the presence of a strong acid or strong base catalyst to create fatty acid esters via a transesterification process, and then converted to the free acid upon addition of a strong acid. As will be shown below, the increase in ALA and LA concentrations facilitate improved biological activity. Further, many commercial chia seed oil compositions, particularly chia seed oil compositions intended for cooking or oral consumption, do not contain ALA and LA as a free acid, but instead included as part of triglyceride.

Furthermore, an enriched chia seed oil composition, hydrolyzed as discussed above, can be admixed with an un-enriched chia seed composition in order to provide the necessary level of stability for the intended application. In a typical application, such as when the chia seed oil is included at relatively low concentrations in a topical formulation, a 1:1 weight ratio of enriched chia seed:un-enriched seed oil can provide the necessary stability over time. If stability is of less concern, the relative amount of enriched chia seed oil composition can be increased to provide a weight ratio of enriched chia seed:un-enriched seed oil of, for example, 1.1, 1.2, 1.3, 1.4, 1.5, 1.6, 1.7, 1.8, 1.9, 2.0 or higher. If stability is of more concern, the relative amount of enriched chia seed oil composition can be decreased to provide a weight ratio of enriched chia seed: un-enriched seed oil of 0.9, 0.8, 0.7, 0.6, 0.5, 0.4, 0.3, 0.2, 0.1 or lower.

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Compositions

In order to determine whether chia seed-derived compositions had differing ability to modulate PP2A activity and to determine which chia plant variety yielded compositions that had the highest modulation effect, various compositions were prepared using the following method:

1000 mL of 80% ethanol (1:10 w/v) was charged to a 4 L, Erlenmeyer flask, followed by addition of 100 g of ground chia seeds. The suspension was stirred for 18 hours at 50° C., then filtered and evaporated to dryness. The mass of the resulting brown oil was calculated, and the oil was resolubilized in 1:10 (w/v) of ethanol (the "Stage 1 Product"). The mixture was filtered, stirred and heated at 75° C. for 1 hour, then slowly cooled to 4° C. for 18 hours, then 20° C. for 2 hours. The resulting suspension was filtered, and evaporated to dryness to give a light brown oil (the "Final Product").

Example 2

Effect on PP2A Methylation

Compositions were created using the extraction methods as generally described in Example 1. These compositions were assayed for their ability to preserve the methylation status of PP2A AC dimer in the presence of protein phosphatase methylesterase-1 (PME-1), using a radioactive filter binding assay.

Protein Purification

PP2A-AC dimer was prepared as previously described in Tolstykh T, Lee J, Vafai S, Stock J B. Carboxyl methylation regulates phosphoprotein phosphatase 2A by controlling the association of regulatory B subunits. EMBO J. 2000; 19(20: 5682-5691. Additional purification was performed with a HiPrep™ 16/60 Sephacryl® S100 HR in a buffer composed of 50 mM MOPS pH 7.2, 1.0 mM EDTA, 1.0 mM dithio-threitol (DTT), and 0.50 μg/ml each of aprotinin, leupeptin and pepstatin. Leucine carboxyl methytransferase-1 (LCMT-1) and Protein phosphatase methylesterase-1 (PME-1) were prepared using the methods as previously described Xing Y, Li Z, Chen Y, Stock J B, Jeffrey P D, Shi Y. Structural mechanism of demethylation and inactivation of protein phosphatase 2A. Cell. 2008; 133(I):154-163.

Demethylation of PP2A by PME-1

[3H]-labeled methylated PP2A AC dirtier was prepared by incubating PP2A, LCMT1 and [3H]-SAM (PerkinElmer; Waltham, Mass.) in 50 mM MOPS-Na (pH 7.2), 5 mM MgCl2, and 1 mM DTT at room temperature for 1 hour. Demethylation of PP2A by PME-1 was measured using the radioactive filter binding assay format. 20 nM PME-1 was incubated for 15 minutes with extract or compound, then 20 nM of [3H]-labeled methylated PP2A AC dimer was added. Reactions were run at room temperature for 30 minutes and then applied to a 96-well filter plate (Millipore Co.) containing 30% TCA where proteins were precipitated and separated from the excess of [3H]-SAM by washing with 70% ethanol. [3H]-incorporation was measured using Top-Count NXT scintillation counter (PerkinEimer; Waltham, MA). $IC_{50}$ values were generated from dose-response curves using a four-parameter logistic curve fit using SigmaPlot software (Systat Software, San Jose, CA).

The following results were obtained:

TABLE 1

PP2A Demethylation Activity of Chia
Seed-Derived Compositions by Source

| I.D. | Sourcing Company | Lot #/ Source | PP2A Demethylation $IC_{50}$ (μg/mL) |
|---|---|---|---|
| NC-1 | Nutiva | Argentina | 3.6 |
| NC-12 | Nutiva | Paraguay | >50 |
| NC-3A | BI Nutraceuticals | B808568 | >50 |
| NC-3B | BI Nutraceuticals | B601507 | >16.7 |
| NC-3C | BI Nutraceuticals | B805524 | >16.7 |
| NC-7 | Inka Seed | ec19001 | 11.8 |
| NC-8 | Pure Leaf | n/a | >50 |
| NC-9 | North Mountain Company | n/a | >50 |
| NC-10 | Food to Live | SO-16399 | >50 |
| NC-11 | Wunder Basket | n/a | >50 |
| NC-15 | SalbaSmart | 171109-01 | 3.6 |
| NC-17 | ChiaSeedsDirect.com | n/a | >50 |
| NC-19A | SalbaSmart | 181203-01 | 18.3 |
| NC-19B | SalbaSmart | SSH01S18/ES6 | — |
| NC-19C | SalbaSmart | SSH01S18/ES7 | — |
| NC-21A | Naturekost de Mexsco | AA-CHNCN-008-81 | >50 |
| NC-21B | Naturekost de Mexico | B-CHNCN-003-81 | >50 |
| NC-22 | Gigawatt | n/a | >50 |
| NC-23 | AgriLatin-Peru | n/a | 5.3 |
| NC-24 | CPX Peru | 168-2019 | >50 |
| NC-27A | Tierra Overseas | CHS01 | — |

TABLE 1-continued

PP2A Demethylation Activity of Chia
Seed-Derived Compositions by Source

| I.D. | Sourcing Company | Lot #/ Source | PP2A Demethylation $IC_{50}$ (μg/mL) |
|---|---|---|---|
| NC-27B | Tierra Overseas | CHS12 | >50 |
| NC-28A | Heartland | 30116-117-X-X | — |
| NC-28B | Heartland | AT-10115-108-X-X | >50 |

<LOQ indicates less than limit of quantitation;
n/a indicates not available;
— indicates not determined.

For comparison, PP2A demethylation activity of commercially sourced chia oil was also tested using the procedures outlined above. No additional processing of the chia oil was performed before testing. The results are shown below:

TABLE 2

PP2A Demethylation Activity of Chia
Oil-Derived Compositions by Source

| I.D. | Sourcing Company | PP2A Demethylation $IC_{50}$ (μg/mL) |
|---|---|---|
| NC-2 | Natural Sourcing Oil | 50 |
| NC-5 | Carrubba Inc Oil Soluble | 29.9 |
| NC-13 | Radiant (Korea) | >50 |
| NC-26 | Botanical Beauty | >50 |
| NC-29 | Erbology | >50 |
| NC-30 | US Organics: Nature to Nature | >50 |

<LOQ indicates less than limit of quantitation;
n/a indicates not available;
— indicates not determined.

As demonstrated by the above data, the highest average demethylation activity was shown by compositions prepared using Salba chia seeds. None of the chia oils tested had comparable activity. Only a single batch of the Nutiva chia seed-derived had comparable demethylation activity, but all other Nutiva batches had negligible activity. Only Salba seed-derived compositions had consistently high demethylation activity.

Notably, Salba chia (Salba Smart Natural Products, Centennial, CO, USA) is one of the few non-GMO chia varieties in the world and is grown in a socially responsible manner. Salba chia is herbicide-free, pesticide-free, gluten-free and free of heavy metals. Salba chia seeds also have demonstrably higher omega-3 and omega-6 polyunsaturated fat content and higher anti-oxidant activity than competing chia seed sources. Moreover, the company's quality control processes ensure a consistent, high quality product across batches and even different years.

Example 3

Linoleic Acid and α-Linolenic Acid HPLC Analyses

Testing for PP2A demethylation activity is time-consuming and expensive. What is needed is an alternative assay method that would be easier to perform and more cost effective. It was hypothesized that PP2A demethylation activity might correlate to the presence of certain compounds in the chia seed compositions. Since it was known from Examples 1 and 2 that Salba chia have high concentrations of linoleic acid (LA or cis,cis-9,12-octadecadienoic acid) and α-linolenic acid (ALA or cis,cis,cis-9,12,15-octa-cedatriencoic acid), it was decided that one of the variables to be tested was LA and ALA concentrations, as well as the ratio of LA to ALA.

HPLC analysis was performed as previously described in Guarrasi V, Mangione M R, Sanfratello V, Martorana V, Butane D. Quantification of underivatized fatty acids from vegetable oils by HPLC with UV detection. J Chromatogr Sci. 2010; 48(8):663-668. Isocratic gradient utilizing acetonitrile:methanol:hexane (90:8:2)+0.02% acetic acid as mobile phase over 35 minutes. Separation was performed on a Luna 5 μm C18(2) 100 Å 250×4.6 at a flow rate of 1 mL/min, monitored at 208 nm on an Agilent 1290 Infinity (Santa Clara, CA). Standard curves of linoleic acid (LA) and α-linolenic acid (ALA) were obtained from Sigma-Aldrich (St. Louis, Mo.) and utilized for quantification.

TABLE 3

LA and ALA Content of Chia Seed-Derived Compositions by Source

| I.D. | ALA Content (μg/mL) | LA Content (μg/mL) |
|---|---|---|
| NC-1 | 35.195 | 10.122 |
| NC-12 | 4.559 | 0.881 |
| NC-3A | 1.734 | 0.332 |
| NC-3B | 3.314 | 1.403 |
| NC-3C | 2.975 | 1.560 |
| NC-7 | 9.912 | 5.108 |
| NC-8 | 2.148 | <LOQ |
| NC-9 | n.d. | — |
| NC-10 | 1.939 | 0.930 |
| NC-11 | n.d. | — |
| NC-15 | 14.938 | 4.427 |
| NC-17 | 1.939 | 0.476 |
| NC-19A | 7.670 | 2.801 |
| NC-19B | 8.931 | 3.540 |
| NC-19C | 5.780 | 1.671 |
| NC-21A | 2.125 | <LOQ |
| NC-21B | 2.213 | <LOQ |
| NC-22 | 0.980 | <LOQ |
| NC-23 | 10.117 | 4.559 |
| NC-24 | 0.940 | <LOQ |
| NC-27A | 0.966 | <LOQ |
| NC-27B | 1.391 | 0.508 |
| NC-28A | 1.224 | 1.151 |
| NC-28B | 2.538 | 0.912 |

<LOQ indicates less than limit of quantitation;
n/a indicates not available;
— indicates not determined

TABLE 4

LA and ALA Content of Chia Oil-Derived Compositions by Source

| I.D. | ALA Content (μg/mL) | LA Content (μg/mL) |
|---|---|---|
| NC-2 | — | — |
| NC-5 | 1.3 | — |
| NC-13 | — | — |
| NC-26 | <0.1 | <LOQ |
| NC-29 | 1.9 | <LOQ |
| NC-30 | <0.1 | <LOQ |

<LOQ indicates less than limit of quantitation;
n/a indicates not available;
— indicates not determined These concentrations represent the free fatty acid content (i.e., ALA or LA) in the composition, and does not include fatty acids that constitute part of a triglyceride. If desired, the amount of free ALA or LA, as found in either a commercial source of chia seed oil or as synthesized, can be increased by the process of Example 14, whereby triglycerides are hydrolyzed to liberate the free fatty acid from triglycerides based on a transesterification reaction with an alcohol in the presence of an acidic or basic catalyst, in a manner analogous to the production of biodiesel from vegetable oils.

Example 4

Selection Criteria Based on Linoleic Acid and α-Linolenic Acid Content

The data shows a clear yet complex correlation between PP2A demethylation activity and LA and ALA concentrations. However, the relationship is non-linear and less than intuitive. One cannot infer PP2A demethylation activity based solely on LA concentration, ALA concentration or even total LA plus ALA content. However, there does appear to be a concentration threshold that would achieve 50% inhibition.

In order to determine the appropriate thresholds that can be used as a proxy for PP2A demethylation activity, compositions comprising LA and ALA in varying ratios and concentrations were tested for PP2A demethylation inhibition.

TABLE 5

Percent Inhibition as a Function of LA and ALA Concentration.

| Ratio ALA:LA | PP2A Demethylation Activity (Percent Inhibition) | |
|---|---|---|
| | 0.5 μg/mL LA | 1 μg/mL LA |
| 0:1 | 28.90 | 60.66 |
| 1:1 | 32.19 | 72.59 |
| 2:1 | 30.84 | 74.81 |
| 3:1 | 30.87 | 78.91 |
| 4:1 | 34.43 | 76.05 |
| 6:1 | 42.87 | 82.57 |
| 8:1 | 50.29 | 82.90 |
| 10:1 | 55.51 | 80.11 |
| 12:1 | 66.19 | 102.89 |

Although the precise relationship between LA and ALA concentrations and PP2A demethylation activity is complex, it is possible to discern a general rule that can be applied to determine whether a chia seed composition is likely to exhibit, 50% PP2A inhibition. Specifically, the conditions necessary to obtain 50% PP2A inhibition can be summarized as follows:

If [LA]=0 μg/mL, then [ALA] must be >8 μg/mL

If [LA]=0.5 μg/mL, then [ALA] must be >4 μg/mL

If [LA]≥1 μg/mL then, then 50% PP2A inhibition is achieved regardless of [ALA]

Notably, at lower concentrations of LA (e.g., 0.5 ug/mL), a 8:1 ratio ALA to LA is needed to achieve 50% inhibition, whereas the prior art literature has indicated that the ratio of ALA to LA found in chia seeds is consistently around 3:1. See, e.g., U.S. Pat. No, 8,652,544 (ALA:LA ratio=3.3:1); Peiretti P G, Gai F (2009), Fatty Acid and Nutritive Quality of Chia (Salvia hispanica L.) seeds and Plant During Growth. Animal Feed Science and Technology 148(2):267-275 (ALA:LA ratio=3:1); Timilsena Y P, Vongsvivut J, Adhikari R, Adhikari B. (2017) Physicochemical and Thermal Characteristics of Australian Chia Seed Oil. Food Chemistry 228:394-402 (ALA:LA ratio 3:1). Concentrations of [ALA] and [LA] above are based on their presence in the composition as free acids, not as a constituent of a triglyceride.

Example 5

Antibacterial Activity

In order to determine whether the compositions of this invention have antibacterial activity, the compositions were assayed for their ability to inhibit the growth of *Cutibacterium acnes* and *Staphylococcus aureus* bacteria

Determination of Minimum Inhibitory Concentration

The inhibition of growth of *Cutibacterium acnes* and *Staphylococcus aureus* bacteria was measured according to the methods described in Nakatsuji et al., J Invest Dermatol, 2009, 129: 2480-2488; Traub and Leonhard, Chemotherapy, 1994; 40(6):374-383. In summary, the strain ATCC® 6919™ of *C. acnes* (American Type Culture Collection, Manassas, VA) was cultured on Reinforced *Clostridium* agar (BD 218081), under anaerobic conditions using Gas-Pak (B D, Sparks, MD) at 37° C. ATCC® 29213™ strain of *S. aureus* was cultured on tryptic soy agar (BD 211825), under aerobic conditions at 37° C. A single colony was inoculated in broth medium and cultured at 37° C.

In addition to various positive controls, both the Final Product and the First Stage Product of the extraction process described in Example 1 were tested as described below. Test material was dissolved in 100% (v/v) DMSO. Doxycycline was dissolved in 100% (v/v) water. Samples of each test material and a solution of doxycycline were then each incubated with an inoculum of bacteria at a concentration of $1 \times 10^6$ CFU per mL, in broth medium in a 96-well microplate (0.1 mL per well) under aerobic conditions for 24 hours (*S. aureus*) or anaerobic conditions for 72 hours (*C. acnes*). Samples of each material were tested at final concentrations per well up to 4 mg/mL. A control well received only 5% (v/v) of DMSO or water. After 24-72 hours incubation, the bacteria cultures in the 96-well microplate were mixed well and then absorbance readings at 600 nm were taken to determine bacterial growth. Bacteria growth curves were plotted and the concentration of each material tested that yielded 90% inhibition (MIC) of bacterial growth was determined.

The results are summarized in the table below:

TABLE 6

Minimum Inhibitory Concentration.

| | MIC (µg\mL) | |
| Material Tested | *Cutibacterium acnes* (ATCC ® 6919 ™) | *Staphylococcus aureus* (ATCC ® 29213 ™) |
| --- | --- | --- |
| Stage 1 Product | >4000 | 2500 |
| Final Product | 562.5 | 241.1 |
| Benzoyl peroxide | 500 | 500 |
| Salicylic Acid | 1000 | 2000 |
| Doxycycline | 0.6 | 0.2 |

The data demonstrates that the Final Product composition created in accordance with Example 1 not only displays significant antimicrobial activity against both *Cutibacterium acnes* and *Staphylococcus aureus* bacteria, but shows superior antibacterial activity compared to salicylic acid, a well-known anti-acne agent. The Final Product also shows significantly superior antibacterial activity compared to the First Stage Product of Example 1 (which demonstrates negligible antibacterial activity), demonstrating that not all chia seed compositions are effective antimicrobial agents.

Doxycycline hydrate (Sigma-Aldrich, St. Louis, MO) and benzoyl peroxide (Fisher Scientific (Hampton, N.H.) demonstrated superior antibacterial activity, but both have significant disadvantages. For example, the antibiotic doxycycline has serious side effects, including nausea, vomiting, diarrhea, loss of appetite, hives, sun sensitivity, and temporary teeth discoloration. Benzoyl peroxide, while extremely effective, can inflame and irritate the skin; indeed, patients with sensitive skin and those suffering from eczema, seborrheic dermatitis or psoriasis are usually warned to avoid long term use of benzoyl peroxide, which dries the skin. Salicylic acid also has common side effects, such as hives, pruritis (itching), peeling skin and stinging/tingling sensation.

Example 6

Determination of Skin Hydration Gene Markers

The effect of the compositions of this invention on gene expression related to skin hydration was measured according to the methods described in Li et al., Dermatology, 2010, 51(2): 106-112; Jiang et al, Exp Dermatol, 2011; 20(7):595-599. In summary, normal human epidermal keratinocytes (NHEKs) from neonatal donors were obtained from ThermoFisher (Carlsbad, CA) and cultured in EpiLife® media supplemented with keratinocyte-growth supplement and 60 µM calcium (ThermoFisher; Carlsbad, CA). Cells were cultured until the second passage and seeded on 6-well plates for 24 hours before treatments.

Both the Final Product and the First Stage Product of the extraction process described in Example 1 were tested as described below. Test materials were dissolved in 100% (v/v) methanol. Samples of each test material were then mixed in culture media without growth factors (2 mL per well) at 37° C. and 5% $CO_2$ for 24 hours. Control wells received only 1% (v /v) of vehicle. After 24 hours incubation, cells were harvested and homogenized by cell scrapers in lysis buffer. Total RNA was extracted using the RNAqueous kit (ThermoFisher; Carlsbad, CA) and cDNA was obtained using the High Capacity RNA-to-cDNA kit (ThermoFisher; Carlsbad, CA). Quantitative PCR (qPCR) was performed using the TaqMan® Fast Advanced Master Mix (ThermoFisher; Carlsbad, CA) and specific TaqMan®-probes human gene primers for AQP3, HAS2 and GAPDH to calculate the relative gene fold expression change per treatment. Gene expression analysis was performed using the comparative Ct method (2-[delta][delta] Ct) approach by comparing the Ct values of the treated scruples with the untreated samples and normalized to GAPDH gene expression as endogenous housekeeping gene.

The results are summarized in the table below:

TABLE 7

Gene Expression Analysis.

| | Percent (%) Gene/GAPDH Expression vs Vehicle-Treated | |
| Material Tested | AQP3 | HAS2 |
| --- | --- | --- |
| Stage 1 Product | 2 | 25 |
| Final Product | 93 | 119 |

Example 7

Human Clinical Trials

A single-blind, single-center clinical trial was conducted with 6 healthy volunteers of either sex to evaluate the moisturization efficacy of a moisturizing cream (formulated as shown below in Table 8) containing the composition prepared using the process of Example 9, vehicle (i.e., the formulation of Table 8 minus the active ingredient—i.e., the chia seed composition), a negative control (untreated), and two positive controls (petroleum jelly and glycerin).

TABLE 8

| Moisturizing Cream | |
| --- | --- |
| Ingredients | w/w % |
| Water | 69.10 |
| Glycerin | 2.00 |
| Pentasodium Pentetate | 0.10 |
| Carbomer | 0.60 |
| Propanediol | 10.00 |
| Xanthan gum | 0.20 |
| Caprylic/Capric Triglyceride | 10.00 |
| Petrolatum | 3.00 |
| Dimethicone | 1.00 |
| Tocopherol | 0.10 |
| *Salvia Hispanica* Seed Composition Prepared in Accordance with the Process of Example 9 | 0.10 |
| Stearyl Alcohol | 0.50 |
| Glyceryl Stearate SE | 1.50 |
| Steareth-20 | 1.50 |
| Potassium Hydroxide | q.s. pH 6 |
| Phenoxyethanol | 0.30 |
| Total | 100.00 |

The objective of this study was to evaluate the moisturization efficacy (as measured by Corneometer®) and to evaluate the relative degree of improvement to skin barrier functionality of two test articles as measured by Trans Epidermal Water Loss (TEWL) assessments when tested in 16 healthy subjects. See, e.g., Johan du Plessis et al., International Guidelines for The In Vivo Assessment Of Skin Properties In Noel-Clinical Settings: Part 2. Transepidermal Water Loss and Skin Hydration, Skin Res. Technol. 19(3), 265-278 (2013); C. W. Blichmann and J. Serup, Assessment of Skin Moisture. Measurement of Electrical Conductance: Capacitance and Transepidermal Water Loss, Acta Derm. Venereol. 68(4): 284-290 (1988).

Inclusion criteria for the subjects of the study were: (a) the subject is a healthy male or female, aged 18 years or older; (b) the subject has signed a written informed consent; (c) no use of any skin treatment products on the lower legs for three days before the active phase and during the actual study; and (d) no washing of the lower legs for three hours prior to coming to the test center. Exclusion criteria for the study were: (a) pregnancy or lactation; (b) inadequate precautions/procedures to prevent pregnancy (women of child bearing potential only); (c) a current skin disease of any type apart from mild facial acne (e.g. eczema, psoriasis); (d) history of malignant disease; (e) heavy alcohol consumption (i.e. more than 14 units per week or 4 units a day); (f) significant past medical history of hepatic, renal, cardiac, pulmonary, digestive, hematological, neurological, locomotor or psychiatric disease; (g) history of asthma requiring regular medication; (h) current use or history of repeated use of illicit drugs; (i) known sensitivity to the test article, similar materials or their constituents; (j) current participation in a clinical trial or follow-up work with the lower legs as the target sites. Restrictions during the study included: (a) subjects must not touch the areas where the test articles have been applied' (b) subjects must refrain from smoking throughout their visit to the test center; (c) subjects must remain in the environmentally controlled room for as long as possible during the study (toilet visits are acceptable, but subjects need to have been in the environmentally controlled room for at least 30 minutes before any assessment); (d) no consumption of hot beverages at any time whilst in the controlled room, or any product containing caffeine in the one hour preceding each assessment; and (e) no treatment of lower legs for three hours before all visits.

On day −3 of the study, subjects were given a bland soap product (e.g., Simple® Soap) to use on their lower legs for the three days prior to the active phase. They were instructed not to use any other treatment products on their lower legs for the next 3 days (the "Washout Phase"). These products included moisturizing foam baths, shower gels or soaps, lotions and creams, and depilatory products. As part of the pre-treatment assessment, subjects sat resting for a period of at least 30 minutes in a controlled environment at a temperature of 22° C.±2° C. and at a relative humidity of 45%±5%. Following the rest period, their lower legs were marked with a total of four 5 cm×5 cm squares.

Moisturization measurements to study the humectant properties of the test articles were performed using the Corneometer® CM825 (Courage and Khazaka, Germany). This instrument relies on the dielectric constant, a physical property of water, which is relatively high and as such will affect the capacitance of a capacitor. Any change in the dielectric constant due to skin moisture variations would alter the capacitance of the precision capacitor in the instrument. These variations were detected electronically and converted into a value by the Corneometer®. A 15-minute warm-up period was allowed before using the Corneometer®.

Following assessments of skin hydration by a Corneometer®, a single application of the test articles (i.e., the chia seed formulation and vehicle alone) was made to the lower leg. Further Corneometer® assessments were then performed at 2, 8, and 24-hours following test article application. Assessments of transepidermal water loss were performed by a Tewameter, followed by the application of the test article, to four marked out squares on the volar forearm of the subjects. Further transepidermal water loss assessments, performed by a Tewameter, were performed at 2, 8, and 24-hours following test article application. Individual Corneometer® values and mean Corneometer® values and statistical analyses comparing the product treated with the untreated test sites for each study time point are presented in this report for the 16 subjects who completed the study.

Individual Tewameter values, mean Tewameter values and statistical analyses comparing sites for each study time point are presented in this report for the 16 subjects who completed the study. Both test articles (i.e., the formulation containing the chia seed composition and vehicle alone) produced statistically significantly higher Corneometer® values (p<0.05) than the negative control at all time points following post treatment times of 2, 8, and 24 hours.

The following results were obtained, shown as mean Corneometer® Values:

TABLE 9

| | | Mean Corneometer ® Values | | |
| --- | --- | --- | --- | --- |
| | 0 hours | 2 hours | 8 hours | 24 hours |
| Composition of Table 8 | 22.5 | 72.2 | 62.4 | 46.1 |
| Vehicle | 22.6 | 64.3 | 56.5 | 32.5 |
| Negative Control (untreated site) | 22.5 | 22.4 | 22.2 | 22.6 |
| Positive Control (glycerine) | 22.7 | 127.1 | 106.8 | 82.3 |

The following statistical analysis results were obtained against the Negative Control (untreated site), p values shown below:

TABLE 10

| | | Statistical Analysis | | |
| --- | --- | --- | --- | --- |
| | 0 hours | 2 hours | 8 hours | 24 hours |
| Composition of Table 8 | 1.00 | $3.28 \times 10^{-17}$ | $1.32 \times 10^{-15}$ | $5.00 \times 10^{-11}$ |
| Vehicle | 0.84 | $5.72 \times 10^{-16}$ | $1.06 \times 10^{-13}$ | $3.59 \times 10^{-7}$ |
| Positive Control (glycerine) | 0.68 | $1.37 \times 10^{-21}$ | $1.60 \times 10^{-19}$ | $1.04 \times 10^{-15}$ |

Statistical Significance if $p < 0.05$

The following results were obtained, shown as mean TEWL values:

TABLE 11

| | | Mean Tewl Values | | |
| --- | --- | --- | --- | --- |
| | 0 hours | 2 hours | 8 hours | 24 hours |
| Composition of Table 8 | 9.91 | 7.76 | 8.05 | 9.11 |
| Negative Control (untreated site) | 9.91 | 9.91 | 9.92 | 9.93 |
| Positive Control (petroleum jelly) | 9.92 | 6.68 | 6.75 | 7.75 |

The following statistical analysis results were obtained against the Negative Control (untreated site), p values shown below:

TABLE 12

| | | Statistical Analysis | | |
| --- | --- | --- | --- | --- |
| | 0 hours | 2 hours | 8 hours | 24 hours |
| Composition of Table 8 | 0.86 | $1.76 \times 10^{-8}$ | $1.68 \times 10^{-8}$ | $3.38 \times 10^{-7}$ |
| Positive Control (petroleum jelly) | 0.28 | $4.09 \times 10^{-10}$ | $5.15 \times 10^{-10}$ | $1.08 \times 10^{-9}$ |

Statistical Significance if $p < 0.05$

The test article containing chia seed composition produced statistically significantly lower TEWL values (p<0.05) and decreased skin dryness than the negative control at all time points following post treatment times of 2, 8, and 24 hours, The data from the Corneometer® measurements demonstrate there were no statistically significant differences (P>0.05) between the test sites and the untreated site prior to application of the test articles. This confirms the validity of the study. After application, the test articles produced statistically significant hydration (moisturization) of the skin (P<0.05) when compared to the untreated site for all the time points, up to and including the 24-hour time point.

The data from the TEWL measurements demonstrate there were no statistically significant differences (P>0.05)

between the test sites prior to application of the test articles. This confirms the validity of the study. After application, the test article containing the chia seed composition produced statistically significant improvements to the skin barrier (P<0.05) when compared to the untreated site for all of the time points, up to and including the 24-hour time point.

Example 8

Additional Processes for Preparing Compositions

While the method of Example 1 was effective in creating compositions useful for inhibiting demethylation of PP2A and could be used in a commercial manufacturing process, the method could be improved. The obtained yields could be improved (e.g., 1-2%), particularly in view of possible inexpensive alternative solvents. What is needed is a process that increases yield, reduces cost and maintains the same PP2A demethylation activity. Towards this end, various solvent systems and process conditions were utilized to determine the optimal process for preparing the compositions of this invention.

Various solvents, extraction conditions and other variables were tested in order to maximize yield, while sufficiently maintaining the ALA and LA levels provided by the composition prepared by process of Example 1. Some of the processes tested include:

Process A

1. Chia (seeds, ground) (10.0 g)
2. EtOH (30 mL), Water (3 mL)
3. Stirring at 50° C., 3 days
4. Filtration, evaporation
5. Oil into the MTBE (50.0 mL)
6. Washing with water
7. Drying over $MgSO_4$
8. Yield 1.0 g (10%)

Process B

1. Chia (seeds, ground) (10.0 g)
2. MTBE (100 mL)
3. Stirring at room temperature, 4 hours
4. Filtration, evaporation
5. Drying in vacuum
6. Yield 3.05 g (30%)

Process C

1. Chia (seeds, ground) (10.0 g)
2. EtOH (100 mL), Water (10 mL)
3. Stirring at 50° C., over night
4. Filtration
5. Solution into the water/brine
6. Oil was separated
7. MTBE (10 ml)
8. Organic was separated
9. Washing with water
10. Drying over $MgSO_4$
11. Yield 0.8 g (8%)

Process D

1. Chia (seeds, ground) (10.0 g)
2. EtOH (80 mL), Water (20 mL)
3. Stirring at 50° C., over night 4. Filtration
5. Evaporation
6. Heptane (100 mL)
7. Organic was separated
8. Washing with water
9. Drying over $MgSO_4$
10. Yield 0.38 g (3.8%)

Process E

1. Chia (seeds, ground) (10.0 g)
2. MTBE (10 mL)
3. Column, pressure, eluent—MTBE
4. Evaporation
5. Drying in vacuum
6. Yield 3.7 g (37%)

Process F

1. Chia (seeds) (10.0 g)
2. DCM (20 mL)
3. Stirring at room temperature over night
4. Filtration
5. Evaporation
6. Drying in vacuum
7. Yield 2.2 g (22%)

Process G

1. Chia (seeds) (10.0 g)
2. Acetonitrile (20 mL)
3. Stirring at rt over night
4. Filtration
5. Evaporation
6. Drying in vacuum
7. Yield 240 mg (24%)

Process H

1. Chia (seeds) (10.0 g)
2. Heptane (20 mL)
3. Stirring at room temperature, 3 h
4. Filtration
5. Evaporation
6. Drying in vacuum
7. Yield 3.2 g (32%)

Process I

1. Chia (seeds) (10.0 g)
2. Acetone (30 mL)
3. Stirring at room temperature, 3 h
4. Filtration
5. Evaporation
6. Drying in vacuum
7. Yield 3.1 g (31%)

Process J

1. Chia (seeds, ground) (100.0 g)
2. MTBE (400 mL)
3. Column, pressure, eluent—MTBE
4. Evaporation
5. Drying in vacuum
6. Yield 400 g (40%)

7. Oil—stirring with charcoal
8. Filtration (Celite® (diatomaceous earth))
9. Colorless oil As can be seen from the above examples, the solvents that produced the highest yields were heptane, acetone and MTBE, with MTBE having the best yield overall. Other issues that needed to be addressed were color and stability. For topical products, the composition ideally would be colorless and would be stable to oxidation and/or degradation. in evaluating manufacturing processes, various filtration steps Were added to evaluate Whether color could be reduced and stability increased.

Example 9

Process for Preparing Compositions

The following process was selected:
1. Add MeCN 3:1 (w/v) to ground chia seed material (e.g., SalbaSmart Premium Ground Salba Chia Seed)
2. Stir for 5-18 hrs at 50° C.
3. Filter the seeds using fiber filter and vacuum pump
4. Evaporate filtrate with vacuum (rotary evaporator) to remove acetonitrile ("First Stage")
5. Solubilize the rest crude oil in MTBE (1:1)
6. Add charcoal (activated) (0.1/1)
7. Stir overnight
8. Filter the mixture through double layer—silica gel/ Celite® (diatomaceous earth)
9. Evaporate filtrate with rotary evaporator
10. Dry to dryness in high vacuum ("Final Stage")

For quality control purposes, the amount of ALA and LA can be measured by HPLC, as described in Example 3 above. The PP2A demethylation activity of the resulting composition can also be assayed in accordance with the procedures described in Example 2 above.

Other solvents can be used for either the first or second stage extraction. The solvent for the first stage should preferentially dissolve ALA and LA relative to other components in chia seed. In certain embodiments, ionic liquids, polar protic solvents and polar aprotic solvents are employed for this first stage. The solvent for the second stage should readily solubilize the oil extracted during the first stage, and the solvent should be easily evaporated under vacuum (e.g. at 40 mmHg) at temperatures less than 45° C. are preferred.

Although other filters may be used, silica gel and diatomaceous earth filters are preferred. Due to the nature of the chia seed oil as well as the absorbent-containing filtrate, glass filters, paper filters and cotton filters were found to be less effective. Preferably, at least two filters are used. In a preferred embodiment, filter comprises a double layer of silica gel and diatomaceous earth filters. The filtration can be accomplished in a single step using a double layer filter or serially in two or more steps through multiple filters.

Example 10

Color and Stability

Color (or lack of any color besides white) is an important commercial property of skincare products and of topical products in general. In addition, stability, including oxidative stability, is an important issue, especially given that the oils present in chia seed may oxidize over time, contributing to the color problem. The prior art approach to address the stability issue has focused on adding antioxidants or other vegetable seed oils to improve the color profile and stability of the final product. See, e.g., Vanesa Y. Ixtaina, Susana M. Nolasco and Mabel C. Tomás, Oxidative Stability of Chia (*Salvia hispanica* L.) Seed Oil: Effect of Antioxidants and Storage Conditions, J Am Oil Chem Soc (2012) 89:1077-1090 (addition of rosemary and green tea extracts, tocopherols, ascorbyl palmitate and their blends to increase oxidative stability); Maria Gabriela Bordon, Silvina Patricia Meriles, Pablo Daniel Ribotta, and Marcela Lilian Martinez, Enhancement of Composition and Oxidative Stability of Chia (*Salvia hispanica* L.) Seed Oil by Blending with Specialty Oils, Journal of Food Science (2010) 00:1-10 (blending of walnut, almond, virgin, and roasted sesame oils with chia oil to increase oxidative stability).

To determine the color attributes of the composition of the Example 9 relative to commercially available chia extracts, spectrophotometric analysis at 450 nm was performed on: the Final Product of Example 9 (batch #39); the First Stage Product of Example 9, and three commercial products sold under trade names Botanical Beauty (Chateau Cosmetics, Miami, Fla.), Erbology (London, UK), and US Organic Group Corp (Englewood Cliffs, NJ). A UV-Visible spectrophotometer (BioMate 3S; Thermo Fisher scientific) was used to study the absorbance characteristics (wavelength range from 200 nm to 800 nm) of these oils. Absorbance at 450 nm is reported below, as light absorbed at this wavelength tends to give oil a yellow looking appearance.

In addition, accelerated stability testing was performed on all of the test articles. All test articles were placed sealed glass vials and incubated at 50° C. Samples were taken at 2 weeks and 8 weeks for spectrophotometric analysis.

Surprisingly, the compositions prepared using the process Example 9 had less color when first prepared, as measured by spectrophotometric analysis at 450 nm, when compared to other chia seed compositions. See Table 9 below. As can be seen from the data, the absorbance of the product of the improved process had a lower absorbance than that of three commercial chia seed products (i.e., the product was closest to colorless) and that of the composition of Example 1. Moreover, the absorbance of the Final Product of the process Example 9 was lower than that of the Stage 1 Product of Example 9.

Even more surprisingly, the stability of the product of Example 9 was initially superior to the stability of the three commercial products. The data shows that the color change (at 50° C.) was the least for the product of Example 9 at week 2. However, at week 8, the Final Product of Example 9 was more yellow than the other products. This suggests that the compositions of this invention should not be stored at high temperatures.

TABLE 13

Absorbance as Measured by Spectrophotometric Analysis at 450 nm

| Product Tested | Absorbance at 450 nm, Initial | Absorbance at 450 nm, 50° C., 2 weeks | Absorbance at 450 nm, 50° C., 8 weeks |
|---|---|---|---|
| Composition of Example 9, Final Stage | 0.069 | 0.075 | 0.303 |
| Composition of Example 9, First Stage | 0.307 | 0.241 | 0.228 |
| Erbology | 0.29 | 0.206 | 0.22 |
| U.S. Organic | 0.465 | 0.300 | 0.316 |
| Botanical | 0.155 | 0.103 | 0.135 |

Example 11

UV Absorption

Figure 2:
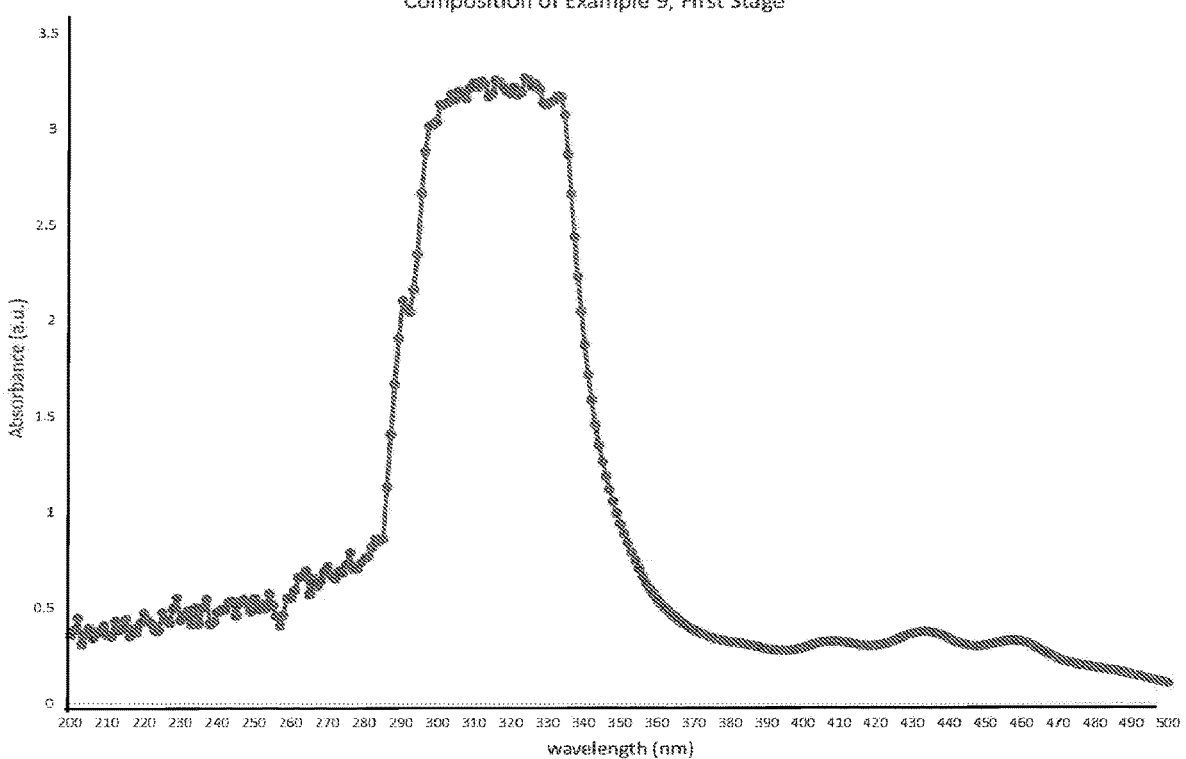
FIG. 2 is a plot of the absorbance (y-axis) at various wavelengths of light (x-axis) of the First Stage Product of Example 9, as described in Example 11.
Figure 3:
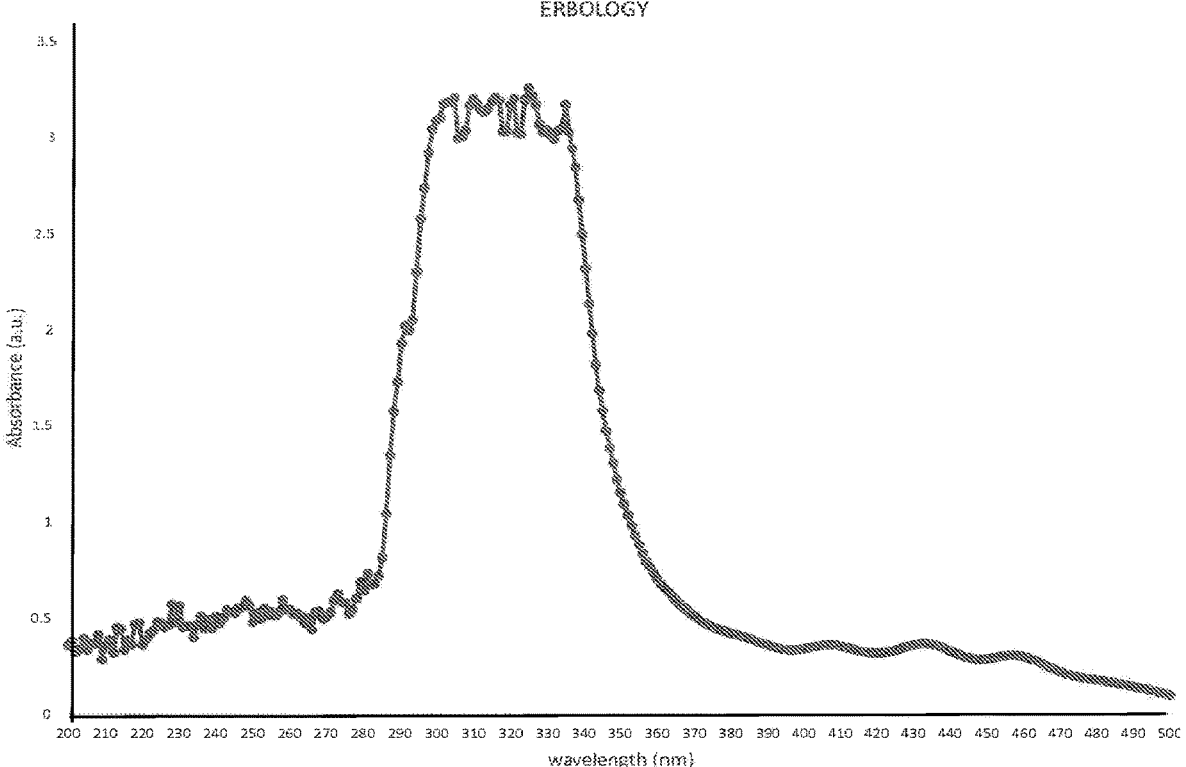
FIG. 3 is a plot of the absorbance (y-axis) at various wavelengths of light (x-axis) of a first "Erbology" commercial composition obtained from chia seeds, as described in Example 11.
Figure 4:
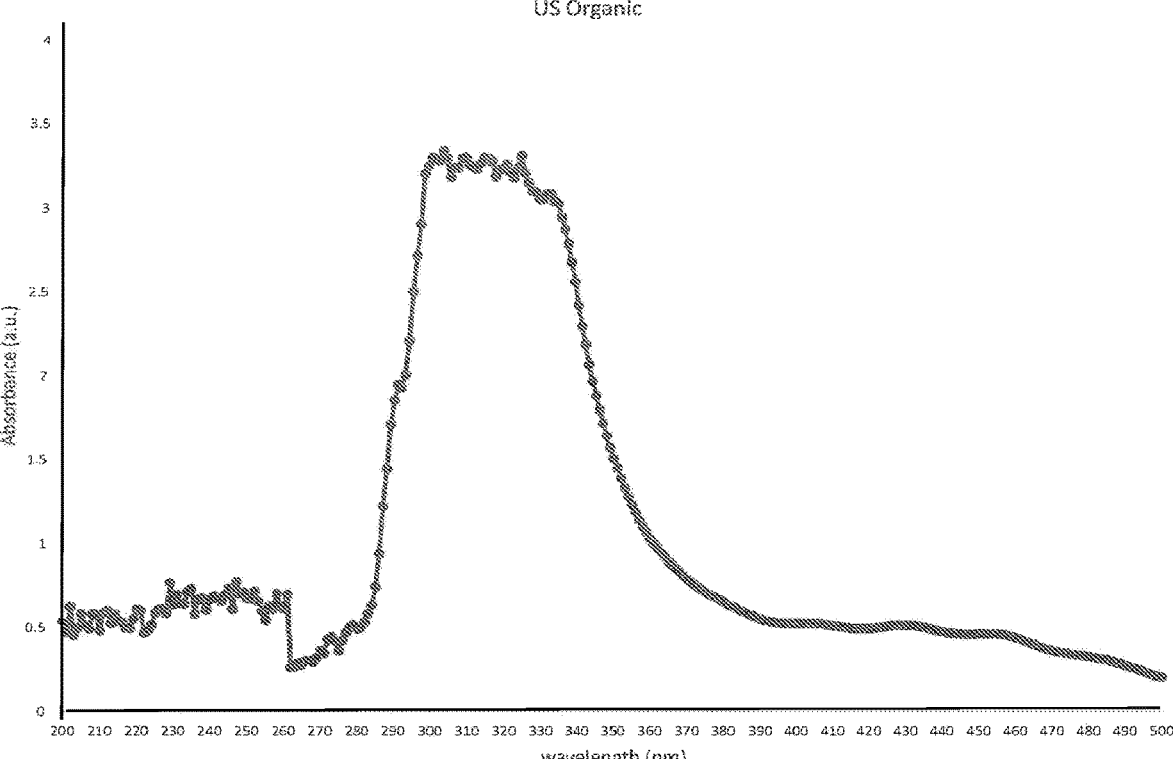
FIG. 4 is a plot of the absorbance (y-axis) at various wavelengths of light (x-axis) of a second "US Organic" commercial composition obtained from chia seeds, as described in Example 11.
Figure 5:
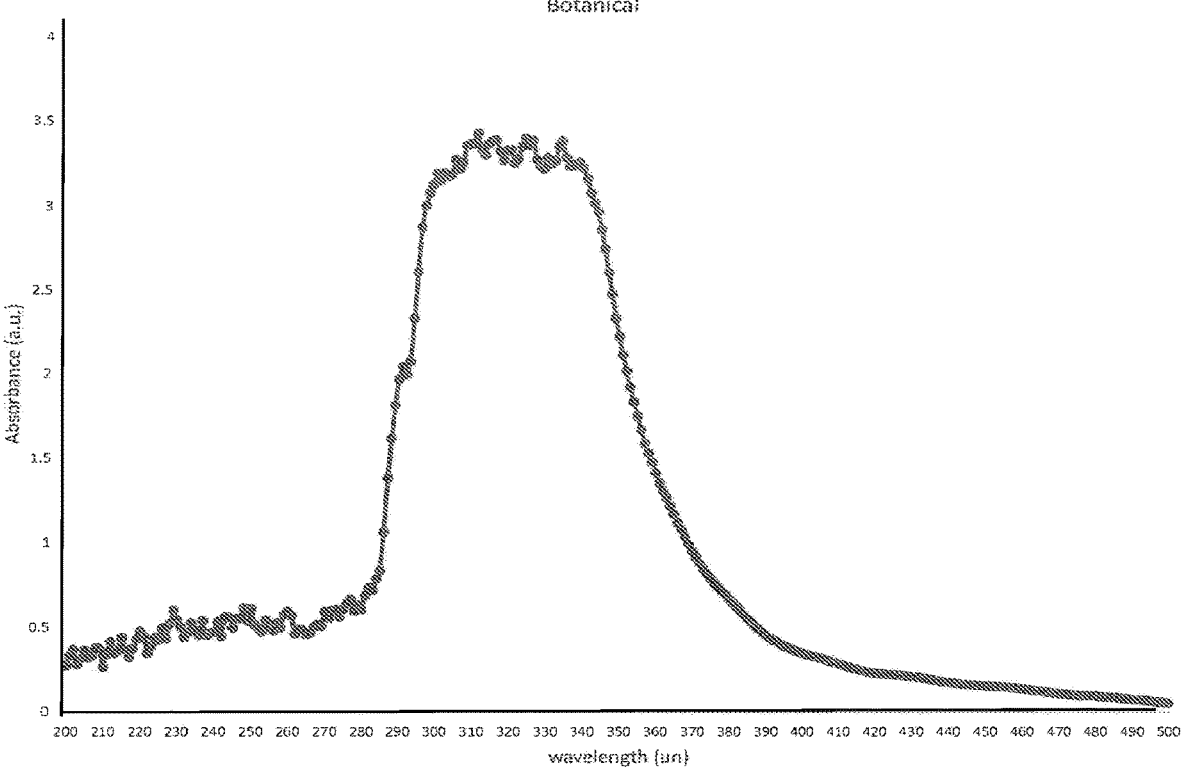
FIG. 5 is a plot of the absorbance (y-axis) at various wavelengths of light (x-axis) of a first third "Botanical" composition obtained from chia seeds, as described in Example 11.

Absorbance data for the compositions set forth above in Table 13 was collected and absorbance (a.u.) as a function of wavelength were plotted. The results are shown in FIGS. 1-5. Surprisingly, the compositions prepared using the improved process and, indeed, all of the chia seed compositions showed very strong absorbance in the UVA range (315-340 nm). Chia seed compositions can be very effective as a functional ingredient in sunscreen products.

Example 12

Testing of Product of Improved Process or Example 9

The product of the improved process was tested for ALA and LA content in accordance with the HPLC analytical methods outlined above, as well as for antimicrobial activity in accordance with the methods described above. For comparison purposes, the ALA and LA content, as well as the antimicrobial activity, of three commercial chia seed oils sold under trade names: Botanical Beauty (Chateau Cosmetics, Miami, FL), Erbology (London, UK), and US Organic Group Corp (Englewood Cliffs, NJ) were also determined using the same methods. The ALA and LA content, as well as the antimicrobial activity, of Stage 1 of the improved process and the Final Product of the process of Example 1 were also determined for comparison. Finally, as positive controls, the antimicrobial activity of benzoyl peroxide (Fisher Scientific), salicylic acid (Fisher Scientific), and doxycycline (Sigma-Aldrich) were also tested. The results are summarized in the table below:

TABLE 14

ALA and LA Content; Minimum Inhibitory Concentration.

| | | | | MIC (μg\mL) | |
|---|---|---|---|---|---|
| Material | Batch No. | ALA % | LA % | Cuti-bacterium acnes (ATCC ® 6919) | Staphylo-coccus aureus (ATCC ® 29213) |
| Final Product* | 39-2 | 8.83 | 1.33 | 500 | 250 |
| Final Product* | 44-1 | 9.53 | 1.30 | 375 | 167 |
| Final Product* | 44-2 | 9.62 | 1.60 | 375 | 167 |
| Final Product* | 69 | 11.18 | 1.97 | 250 | 167 |
| Final Product* | 130 | 0.00 | 0.00 | >4000 | 3000 |
| Stage 1 Product* | 67-1 | 0.05 | 0.00 | >4000 | 1500 |
| Botanical Beauty | N/A | 0.00 | 0.00 | >4000 | 2667 |
| Erbology | N/A | 0.00 | 0.00 | >4000 | 2000 |
| US Organics | N/A | 0.00 | 0.00 | >4000 | 2000 |
| Benzoyl peroxide | N/A | N/A | N/A | 500 | 500 |
| Salicylic Acid | N/A | N/A | N/A | 500 | 2000 |
| Doxycycline | N/A | N/A | N/A | 0.6 | 0.2 |

*Product of Example 9 process
**Product of Example 1 process

As can be seen from the data presented above, with the exception of one batch (Batch No. 130), the compositions of the improved process have consistently high ALA and LA content. (It is likely that the batch in question was defective because of problems in the manufacturing process or in the storage conditions prior to testing.) All of the compositions, again with the exception of defective Batch No. 130, show strong antimicrobial activity against both *C. acnes* and *S.*

*aureus*. In contrast, none of the commercial chia seed oils had detectable levels of ALA or LA. Moreover, the commercial chia seed oils showed no detectable antimicrobial activity towards *C. acnes* and only very weak antimicrobial activity towards *S. aureus*.

Notably, the product of the first step of the improved process (the "Stage 1 Product") had negligible levels of ALA and LA. Similar to the commercial chia seed oils, the Stage 1 Product of the improved process demonstrated no detectable antimicrobial activity towards *C. acnes* and only very weak antimicrobial activity towards *S. aureus*. Furthermore, the Final Product of the process of Example 1 also possessed no detectable antimicrobial activity towards *C. acnes* and only very weak antimicrobial activity towards *S. aureus*. The data clearly demonstrates that the properties and activity of the composition are critically dependent on the extraction and manufacturing process.

Example 13

Topical Formulations

The compositions of this invention can easily be formulated into topical formulations for use in skincare applications. For example, the following creams were formulated according the following recipe:

TABLE 15

Anti-Aging Cream

| Ingredients | w/w % |
|---|---|
| Water | 77.55 |
| Glycerin | 5.00 |
| Pentylene Glycol | 3.00 |
| Pentasodium Pentatate | 0.10 |
| Agar | 0.10 |
| Ammonium Acryloyldimethyltaurate/VP Copolymer | 1.30 |
| Propanediol | 10.00 |
| Sodium Hyaluronate | 0.20 |
| Caprylic/Capric Triglyceride | 2.00 |
| Retinol | 0.10 |
| Tocopherol | 0.10 |
| *Salvia Hispanica* Seed Extract | 0.10 |
| Ceramide NP | 0.05 |
| FirmAct - Seaweed mix | 0.10 |
| Phenoxyethanol | 0.30 |
| Citric Acid | q.s. pH 6 |
| Total | 100.00 |

TABLE 16

Skin Lightening Serum

| Ingredients | w/w % |
|---|---|
| Ethoxydiglycol | 45.95 |
| Water | 20.00 |
| Ascorbic Acid | 15.00 |
| Propanediol | 10.00 |
| Betaine | 3.00 |
| Glycerin | 2.00 |
| PPG-13-Decyltetradeceth-24 | 2.00 |
| Tocopherol | 1.00 |

TABLE 16-continued

Skin Lightening Serum

| Ingredients | w/w % |
|---|---|
| Acetyl Arctigenin | 0.50 |
| Disodium S-Phytyl Diglycoloylcysteine | 0.25 |
| Sodium Hyaluronate | 0.10 |
| Ferulic Acid | 0.10 |
| *Salvia Hispanica* Seed Extract | 0.10 |
| Total | 100.00 |

Example 14

Process for Preparing Chia Seed Extract with Enriched Free Acid

To a 5 liter 3-neck flask equipped with an over-head stirrer, stir shaft, paddle and thermometer, 1000 grams of chia seed oil (Pharma Resources Int'l.) is added at room temperature. As an alternative, any one of the instantly disclosed methods, such as those disclosed in Example 1 and Example 9, may instead be employed to provide the 1000 grams of chia seed extract oil from chia seeds. Following the addition of the oil, 1 liter of reagent grade ethanol (95%, [CAS 64-17-5], Mercedes Scientific) is added to the oil and the resulting mixture is gently stirred at room temperature. While stirring, 1 liter of a 5N sodium hydroxide solution (99%, CAS [1310-73-2], Fisher Scientific) is added to the mixture in a single portion. The resulting biphasic mixture is gently stirred for 18 hours to give an orange solution, which is then acidified to pH 2 with concentrated hydrochloric acid (36%, CAS [7647-01-0], Fisher Scientific). The resulting mixture is transferred to a separatory funnel, allowed to settle, and the aqueous layer is removed to provide an enriched oil with increased amounts of ALA and LA available as a free acid. The free acid enriched oil is diluted with 1000 grams of chia seed oil, then washed two times more with 1 liter of water. The resulting yellow oil is dried over anhydrous sodium sulfate (99%, CAS [7757-82-6], Fisher Scientific) and filtered.

Example 15

Lipolysis Analysis of Chia Seed Extract of Example 1

Lipolysis is the process in which triglycerides (TG) are hydrolyzed into glycerol and free fatty acids. This process releases free fatty acids (FFA) into the bloodstream where they may be either re-esterified by the adipocyte or travel to other tissues and exert other effects throughout the body. The purpose of this study was to evaluate the lipolysis via measure of the glycerol molecule released in lipolysis process. Here, we evaluated the potential capacity of the chia seed extract composition of Example 1 in cultured human pre-adipocyte cells. Cells were seeded in medium and incubated for 7 days. Neat solutions of the enriched free acid chia seed extract composition of Example 1 were prepared formulated in methanol. Cells were pre-treated for 8 hours with or without test material in media. As shown below, the enriched free acid chia seed extract composition of Example 1 at 0.01-0.1%% significantly induced lipolysis after 8 hours.

A Lipolysis Assay Kit (Cat. No. Lip-1) was obtained from Zen-Bio, Inc. (Research Triangle, NC) and used to determine glycerol levels (µM) based on the methodology described below. Glycerol released to the medium is phosphorylated by adenosine diphosphate (ATP) forming glycerol-1-phosphate (G-1-P) and adenosine-5'-diphosphate (ADP) in the reaction catalyzed by glycerol kinase. G-1-P is then oxidized by glycerol phosphate oxidase to dihydroxyacetone phosphate (DAP) and hydrogen peroxide. A quinoeimine dye is produced by the peroxidase catalyzed coupling of 4-aminoantipyrine (4-AAP) and sodium N-ethyl-N-(3-sulfopropyl)m-anisidine (ESPA) with hydrogen peroxide, which shows an absorbance maximum at 540 nm. The increase in absorbance at 540 nm is directly proportional to glycerol concentration of the sample. PDE inhibitors increase intracellular cAMP levels. 3-isobutyl-1-methylxanthine (IBMX), a non-specific inhibitor of cAMP phosphodiesterases (PDE), is used as the positive control.

The following results were obtained:

TABLE 17

Glycerol Levels

| | Glycerol Levels (µM) | | |
| Test Group | Avg | SEM | Fold Improvement |
| --- | --- | --- | --- |
| Untreated | 1.38 | 0.3 | NA |
| Vehicle | 2.5 | 0.2 | 1.8 |
| 100 µM IBMX | 8.8* (p < 0.01 compared to untreated) | 2.3 | 6.4 |
| 0.01% Composition of Example 14 | 29.3* (p < 0.01 compared to untreated) | 1.3 | 11.7 |
| 0.1% Composition of Example 14 | 91.2* (p < 0.01 compared to untreated) | 3.0 | 36.5 |

*p values determined by Student's t-Test using two-tailed distribution and two-sample unequal variance Example 16

In Vitro Antibacterial Analysis of Chia Seed Extract with Enriched Free Acid on Skin-Relevant Strains Our skin microbiome houses billions of microbes, many of which are commensal and beneficial, however in some instances can trigger harmful skin inflammation. The potential for compounds to promote a healthy skin microbiome by targeting the "bad" bugs and not harming the "good" bugs is an emerging field of study in dermatology. The purpose of this study was to evaluate the antibacterial activity of the Chia seed extract composition of Example 14 compared to control Doxycycline applied in vitro to planktonic bacteria categorized as "good" (*M. luteus* ATCC® 4698™, *S. hominis* ATCC® 27847™, *S. warneri* ATCC® 27836™, *S. epidermidis* ATCC® 12228™, *S. capitis* ATCC®27841™, *S. simulans* ATCC® 27850™) and another six which are categorized as "bad" (*S. aureus* ATCC™ 29213™, *S. aureus* MRSA ATCC® 33592™, *S. pyogenes* ATTC® 19615™, *C. acnes* ATCC™ 6919™, *C. xerosis* ATCC® 373™, *C. granulosum* ATCC® 25564™).

Test agents and control were stored at recommended storage temperature until use. Minimum Inhibitory Concentrations (MIC) were determined in vitro using the broth microdilution method. Live cultures of bacteria strains obtained from the American Type Culture Collection (ATCC) and were vehicle-only treated or received applications of test agents at 0.05-500 µg/mL dilution final concentrations. Antimicrobial activity was defined as the lowest concentration of each test material that inhibited ≥85% of the optical density (OD) measured in broth media. Antimicrobial activity was validated using doxycycline hyclate (Sigma-Aldrich; Cat. No. D0891; Lot #0001413638) as positive control.

The following results were obtained:

TABLE 18

Summary Results of Antibacterial Assays

| | | MIC, µg/mL (% w/v)* | |
| | Bacteria Strain | Doxycycline hyclate | Composition of Example 14 |
| --- | --- | --- | --- |
| "Bad" skin bacteria | *S. aureus* ATCC ® 29213 ™ | 0.20 ± 0.00 (0.00002) | 250 (0.025) |
| | *S. aureus* MRSA ATCC ® 33591 ™ | 20.83 ± 7.22 (0.0020) | >500 (>0.05) |
| | *S. pyogenes* ATCC ® 19615 ™ | 0.11 ± 0.07 (0.00001) | 11.72 ± 5.52 (0.0012) |
| | *C. acnes* ATCC ® 6919 ™ | 0.26 ± 0.11 (0.00003) | 532 (0.05) |
| | *C. xerosis* ATCC ® 373 ™ | 0.33 ± 0.11 (0.00003) | 62.50 ± 0.00 (0.0063) |
| | *C. granulosum* ATCC ® 25564 ™ | 0.13 ± 0.06 (0.00001) | >500 (>0.05) |
| "Good" skin bacteria | *M. luteus* ATCC ® 4698 ™ | 0.10 ± 0.00 (0.00001) | 32.55 ± 29.32 (0.0033) |
| | *S. hominis* ATCC ® 27847 ™ | 10.42 ± 3.61 (0.0010) | >500 (>0.05) |
| | *S. warneri* ATCC ® 27836 ™ | 0.31 ± 0.41 (0.00003) | >500 (>0.05) |
| | *S. epidermidis* ATCC ® 12228 ™ | 1.30 ± 0.45 (0.00013) | >500 (>0.05) |
| | *S. capitis* ATCC ® 27841 ™ | 0.65 ± 0.23 (0.00007) | >500 (>0.05) |
| | *S. simulans* ATCC ® 27850 ™ | 1.04 ± 0.45 (0.00013) | 31.25 ± 0.00 (0.0031) |

*Data represents Mean ± StDev from three (3) independent experiments. MIC (Minimal Inhibitory Concentration)

Results produced by visible turbidity and OD changes for each test material showed different antibacterial capacities. Doxycycline hyclate (used as positive control provided strong antibacterial activity for "bad" strains (MIC=0.1-20.8 μg/mL) and "good" strains (MIC=0.1-10.4 μg/mL). The chia seed extract composition of Example 14 also provided strong antibacterial activity for "bad" strains (MIC=12-500 μg/mL). Excluding *M. luteus* and *S. simulans*, HyVia™ didn't affect growth of the "good" skin bacteria strains (MIC>500 μg/mL).

Example 17

In Vitro Anti-Blue Light Induced Phototoxicity of Chia Seed Extract in HaCaT Cells The purpose of this Example was to evaluate the anti-blue light phototoxicity potential capacity of chia seed extract in cultured human keratinocyte cells (HaCaTs) (AddexBio Technologies Cat. No. T0020001). The MTS reduction assay was performed to measure cellular toxicity based on the comparison of the cell protection effect of a test substance when pre-treated before exposure to cytotoxic dose of blue light at 420 nm (480 J/cm$^2$). Cells were seeded in DMEM with 10% FBS and incubated for 24 hours. Neat solutions of the chia seed extract of Example 1 were prepared at 2.5 mg/mL formulated in methanol. Cells were pre-treated for 48 hours with or without test material in FBS-depleted DMEM media. Later, test material was removed from cells and washed with Earle's Buffer Saline Solution (EBSS) and incubated in dark or irradiated with blue light source (1.5 mW/cm$^2$) with a peak spectrum of 420 nm and was irradiated for 53 minutes 20 cm away from the cell culture plate. After irradiation, cellular toxicity and viability was assessed from MTS method expressed as a concentration-dependent reduction of tetrazolium compound [3-(4,5-dimethylthiazol-2-yl)-5-(3-carboxymethoxy-phenyl)-2-(4-sulfophenyl)-2H-tetrazolium, inner salt; MTS]. The quantity of formazan product as measured by the amount of 490 nm absorbance is directly proportional to the number of living cells in culture post-blue light irradiation and incubation with test materials. Skin film protection effect of chia seed extract was determined via the calculation of cell viability in the absence (−blue light) and presence (+blue light) of irradiation. According to this model, a test material is considered to have anti-blue light skin film protection if the ratio of added/non-added materials to cell activity was ≥1.5.

$$A = \frac{CVd1 - CVc1}{CVc0 - CVc1}$$

Where: A is the ratio of added/neon-added materials for cell activity protection; CVd1 is the cell viability value of the group with the added material; CVc1 is the cell viability value of the group without test material; CVc0 is the cell viability value of non-irradiated group (blank control group) without material.

Results showed that chia seed extract (≤2.5 μg/mL) produced a significant increase of cellular viability response compared to untreated cells+/−blue light with A≥1.5. Based on these data, it was concluded that chia seed extract formulated in methanol was skin film protective when comparing cell viability in the absence and presence of blue light-irradiation.

TABLE 19

Cell Viability Results after Chia Seed Extract treatments and Blue light (420 nm) irradiation in HaCaT cells

| Chia Seed Extract [μg/mL] | - Blue Light | | | | | | Ratio of added/ non-added material |
|---|---|---|---|---|---|---|---|
| | AVG | StDev | p Value* | AVG | StDev | p Value* | |
| 0 | 100 | 2 | | 58 | 8 | | |
| 0.16 | 141 | 12 | 0.01 | 168 | 39 | 0.04 | 2.6 |
| 0.31 | 147 | 12 | <0.01 | 172 | 39 | 0.03 | 2.7 |
| 0.63 | 152 | 18 | 0.02 | 173 | 36 | 0.02 | 2.7 |
| 1.25 | 162 | 19 | 0.01 | 171 | 32 | 0.02 | 2 7 |
| 2.5 | 168 | 19 | 0.01 | 140 | 27 | 0.04 | 1.9 |

Data represent cumulative averages from 3 independent experiments.

*p Values were determined by Student's t-Test using two-tailed distribution and two-sample unequal variance. Significance (p Value) compared to untreated cells

Example 18

Prophetic Examples

Other potential formulations that could hypothetically be created include an anti-acne toner, an anti-acne gel, an anti-aging lotion and a skin-lightening face mask. See Tables 20 to 23 below.

TABLE 20

Anti-Acne Toner

| Ingredient Name (INCI name) | w/w % |
|---|---|
| Water | 76.30 |
| Glycerin | 2.00 |
| Methylparaben | 0.20 |
| Tocopheryl Acetate | 0.10 |
| PPG-13-Decyltetradeceth-24 | 1.00 |
| Salicylic acid | 0.10 |
| Butylene Glycol | 10.00 |
| Sodium Hyaluronate | 0.10 |
| Xanthangum | 0.10 |
| *Salvia Hispanica* Seed Extract | 0.10 |
| *Hamamelis Virginiana* (Witch Hazel) Bark/Leaf Extract | 10.00 |
| Potassium Hydroxide | q.s. pH 6 |
| Total | 100.00 |

TABLE 21

Anti-Acne Gel

| Ingredient Name (INCI name) | w/w % |
|---|---|
| Water | 75.65 |
| Glycerin | 2.00 |
| Methylparaben | 0.20 |
| Disodium EDTA | 0.05 |
| Carbomer | 0.60 |
| Tocopheryl Acetate | 0.10 |
| PPG-13-Decyltetradeceth-24 | 1.00 |
| Salicylic acid | 0.10 |
| Butylene Glycol | 10.00 |
| Xanthangum | 0.20 |
| *Salvia Hispanica* Seed Extract | 0.10 |
| *Hamamelis Virginians* (Witch Hazel) Bark/Leaf Extract | 10.00 |
| Potassium Hydroxide | q.s. pH 6 |
| Total | 100.00 |

TABLE 22

Anti-Aging Lotion

| Ingredient Name (INCI name) | w/w % |
|---|---|
| Water | 74.25 |
| Glycerin | 5.00 |
| Disodium EDTA | 0.05 |
| Xanthangum | 0.10 |
| Ammonium Acryloyldimethyltaurate/VP Copolymer | 0.80 |
| Propanediol | 10.00 |
| Sodium Hyaluronate | 0.20 |
| Caprylic/Capric Triglyceride | 3.00 |
| Dimethicone | 1.00 |
| Tocopheryl Acetate | 0.10 |
| Retinol | 0.10 |
| *Salvia Hispanica* Seed Extract | 0.10 |
| Hydroxyethyl Urea | 5.00 |
| Phenoxyethanol | 0.30 |
| Total | 100.00 |

TABLE 23

Skirt Lightening Face Mask

| Ingredients (INCI name) | w/w % |
|---|---|
| Water | 86.60 |
| Pentasodium Pentetate | 0.10 |
| Ammonium Acryloyldimethyltaurate/VP Copolymer | 0.70 |
| Butylene Glycol | 3.00 |
| Glycerin | 5.00 |
| Sodium Hyaluronate | 0.10 |
| PEG-40 Hydrogenated Castor Oil | 1.00 |
| Tocopheryl Acetate | 0.05 |
| Diethyl Sebacate | 2.00 |
| Ferulic Acid | 0.10 |
| 3-O-Ethyl Ascorbic Acid | 1.00 |
| *Oenothera Biennis* (Evening Primrose) Seed Extract | 0.10 |
| *Salvia Hispanica* Seed Extract | 0.10 |
| Phenoxyethanol | 0.15 |
| Total | 100.00 |

All publications, patent and patent applications mentioned in this specification are incorporated herein by reference to the same extent as if each individual publication, patent or patent application was specifically and individually incorporated by reference.

While this invention has been particularly shown and described with references to preferred embodiments thereof, it will be understood by those skilled in the art that various changes in form and details can be made therein without departing, from the scope of the invention encompassed by the appended numbered embodiments. Further, all embodiments included herein are given solely for the purpose of illustration and are not to be construed as limitations of the present invention, as many variations thereof are possible without departing from the spirit and scope of the invention.

What is claimed is:

1. A method of preparing an extract from chia seeds, said method comprising:
   a) introducing acetonitrile to chia seeds to form a mixture;
   b) agitating the mixture at a maintained temperature above room temperature for a period of time;
   c) filtering the chia seeds from the agitated mixture;
   d) evaporating the filtered mixture under reduced pressure to remove the acetonitrile and to form a crude chia seed oil;
   e) introducing methyl t-butyl ether to the crude chia seed oil to form a solution;
   f) adding a decolorant to the solution;
   g) agitating the solution containing the decolorant for a second period of time;
   h) filtering the decolorant from the agitated solution; and
   i) evaporating the methyl t-butyl ether from the filtered solution under reduced pressure, thereby preparing the extract,
   wherein relative to the crude chia seed oil, the extract comprises one or more of the following:
   an increased amount of cis, cis-9, 12-octadecadienoic acid (LA);
   an increased amount of cis, cis, cis-9, 12, 15-octadecatrienoic acid (ALA); and/or
   increased stability and reduced color change when stored at 50° C. for up to eight weeks.

2. The method of claim 1, wherein the ratio of the acetonitrile-to-chia seed is from about 2:1 to about 4:1 (w/v).

3. The method of claim 2, wherein the ratio of the acetonitrile-to-chia seed is about 3:1 (w/v).

4. The method of claim 1, wherein the mixture is agitated for at least 12 hours and the maintained temperature is at least 40° C.

5. The method of claim 1, wherein the mixture is evaporated under reduced pressure with a rotary evaporator to form the crude chia seed oil.

6. The method of claim 1, wherein the methyl t-butyl ether is removed using vacuum evaporation at room temperature.

7. The method of claim 1, wherein the decolorant is an absorbent.

8. The method of claim 7, wherein the absorbent is selected from the group consisting of activated carbon, silica gel, decolorizing clay and activated alumina.

9. The method of claim 8, wherein the absorbent is fuller's earth decolorizing clay.

10. The method of claim 8, wherein the absorbent is activated carbon.

11. The method of claim 1, wherein the solution is agitated with the decolorant for at least 8 hours.

12. The method of claim 1, wherein the decolorant is filtered from the solution.

13. The method of claim 12, wherein the decolorant is filtered from the solution using at least two filters.

14. The method of claim 1, wherein the absorbent is filtered from the solution serially with at least two filters.

15. The method of claim 14, wherein at least one of the filters is a diatomaceous earth filter.

16. The method of claim 14, wherein at least one of the filters is a silica gel filter.

17. The method of claim 1, wherein the solution is evaporated under reduced pressure with a rotary evaporator.

18. The method of claim 1, further comprising grinding the chia seeds prior to introducing the acetonitrile.

\* \* \* \* \*